(12) United States Patent
Kim et al.

(10) Patent No.: US 9,540,421 B2
(45) Date of Patent: Jan. 10, 2017

(54) MITOCHONDRIA TARGETING PEPTIDE

(71) Applicant: UNIVERSITY-INDUSTRY COOPERATION GROUP OF KYUNG HEE UNIVERSITY, Yongin-si (KR)

(72) Inventors: Young Mi Kim, Seoul (KR); Young Cheol Kang, Gunpo-si (KR); Yong Hee Kim, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 29 days.

(21) Appl. No.: 14/424,762

(22) PCT Filed: Aug. 30, 2013

(86) PCT No.: PCT/KR2013/007809
§ 371 (c)(1),
(2) Date: Jun. 26, 2015

(87) PCT Pub. No.: WO2014/035179
PCT Pub. Date: Mar. 6, 2014

(65) Prior Publication Data
US 2015/0361140 A1  Dec. 17, 2015

(30) Foreign Application Priority Data
Aug. 31, 2012 (KR) .................. 10-2012-0096446

(51) Int. Cl.
| | | |
|---|---|---|
| *C07K 14/005* | (2006.01) | |
| *C07K 14/825* | (2006.01) | |
| *C12N 9/08* | (2006.01) | |
| *C12N 9/02* | (2006.01) | |
| *C12N 9/12* | (2006.01) | |
| *C12N 9/00* | (2006.01) | |
| *C07K 7/06* | (2006.01) | |
| *C07K 7/08* | (2006.01) | |
| *A61K 38/00* | (2006.01) | |

(52) U.S. Cl.
CPC ............. *C07K 14/005* (2013.01); *C07K 7/06* (2013.01); *C07K 7/08* (2013.01); *C07K 14/825* (2013.01); *C12N 9/0065* (2013.01); *C12N 9/0089* (2013.01); *C12N 9/1205* (2013.01); *C12N 9/93* (2013.01); *A61K 38/00* (2013.01); *C07K 2319/10* (2013.01); *C07K 2319/21* (2013.01)

(58) Field of Classification Search
None
See application file for complete search history.

(56) References Cited

U.S. PATENT DOCUMENTS

2007/0086981 A1   4/2007  Meijer et al.

FOREIGN PATENT DOCUMENTS

| KR | 10-2010-0086164 A | 7/2010 |
| KR | 10-2011-0058705 A | 6/2011 |
| WO | 2007071962 A1 | 6/2007 |

OTHER PUBLICATIONS

ChemPages 2016 "Biomolecules: Protein 1" accessed from chem. wisc.edu (excerpt only).*
Farmer 2015 "Hematopoietic cytokines as therapeutic players in early stages of parkinson's disease" Front Aging Neuro 7(126):1-5.*
Sigma 2016 "Amino acids reference chart" accessed from sigmaaldrich.com (excerpt only).*
STN Results 2016 accessed from Registry database (see search notes; excerpt only).*
Wikipedia 2016 "Amino acid" accessed from wikipedia.org (exceprt only).*
Journal of the American Heart Association, Jun. 15, 2012, vol. 1, Article No. e001644 (pp. 1-13).
Journal of Biotechnology, Computational Biology and Bionanotechnology, 2011, vol. 92, No. 4, pp. 321-335.
Experimental Cell Research, 2008, vol. 314, No. 1, pp. 103-114.
Movement Disorders, 2010, vol. 25, No. 11, pp. 1670-1764.
Biochimica et Biophysica Acta, Ebub Oct. 19, 2011, vol. 1822, No. 5, pp. 639-649.
Proc. NatL Acad. Sci. USA, vol. 79, pp. 2301-2304, Apr. 1982.
Diabetes, vol. 51, Jan. 2002.
BioMetals, 2005, 18:305-312.

* cited by examiner

*Primary Examiner* — Adam M Weidner
(74) *Attorney, Agent, or Firm* — Lei Guo; Abel Law Group, LLP

(57) ABSTRACT

The present invention relates to a mitochondria targeting peptide, a fusion protein in which the peptide is bound to the carboxyl terminus of a protein transduction domain, a fusion protein in which the peptide is bound to the carboxyl terminus of a protein transduction domain and an antioxidant is bound to the carboxyl terminus of the peptide, an antioxidant composition and a composition for preventing or treating Parkinson's disease including the fusion protein in which the antioxidant is bound, a recombinant polynucleotide in which a polynucleotide coding a protein transduction domain, a polynucleotide coding the peptide, and a polynucleotide coding an antioxidant protein are sequentially bound, to an expression vector including the polynucleotide, and to a transformed host cell including the expression vector.
The mitochondria targeting peptide according to the present invention targets mitochondria with high efficiency not only when the peptide exists alone but also when the peptide is bound to a protein transduction domain and/or to an antioxidant. Further, the peptide has a small size and is thus a very suitable targeting carrier. The peptide becomes processed when introduced into mitochondria, and thus stably delivers the drug carried by the peptide.

18 Claims, 12 Drawing Sheets

Fig. 2
A
YGRKKRRQRRR LLRAALRK_AAL  (SEQ ID NO: 24)
B
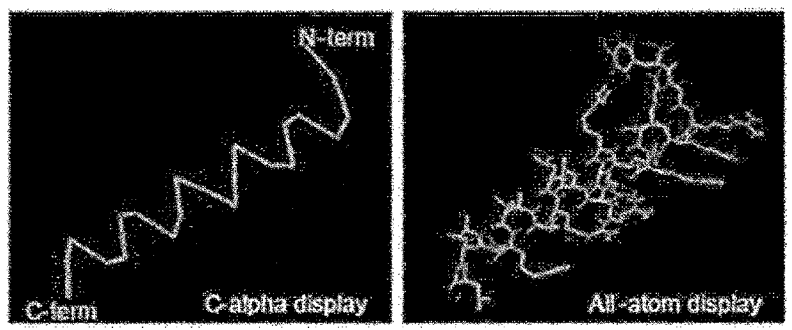
C
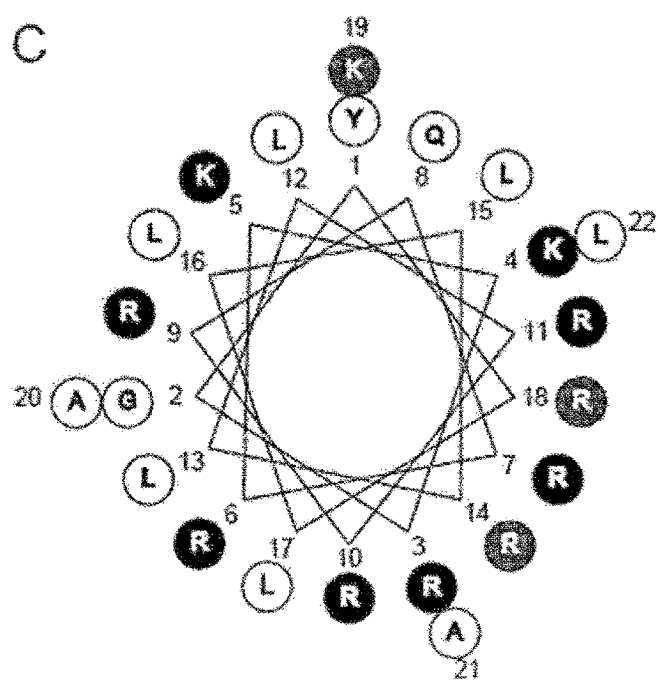

Fig. 3
A
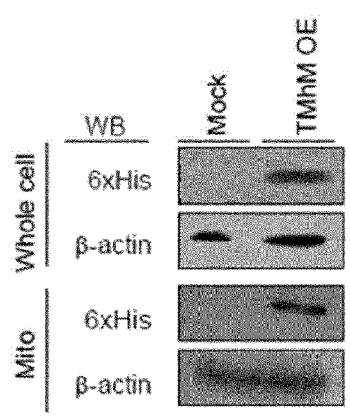
B
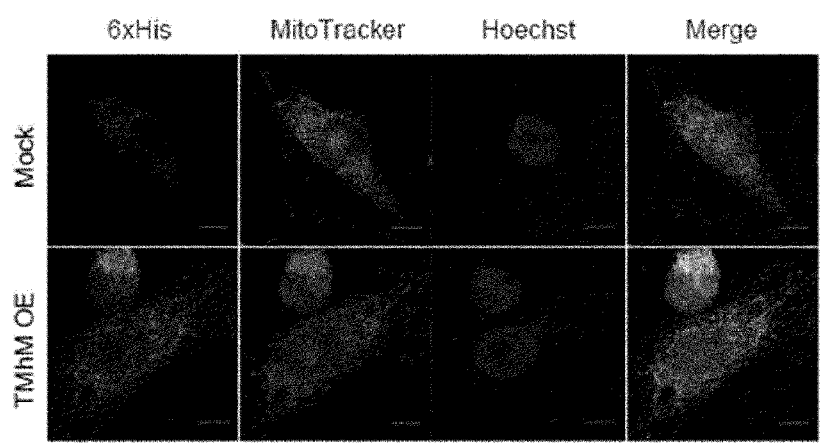

Fig. 15
A 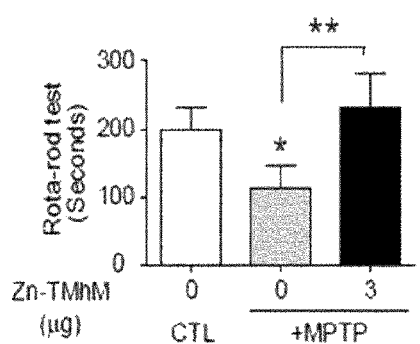
B 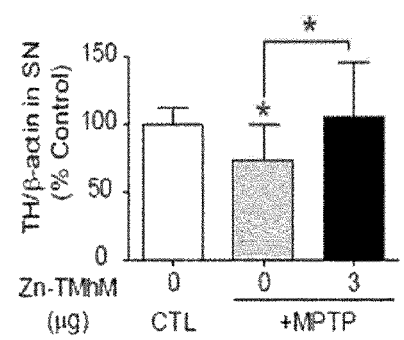
C 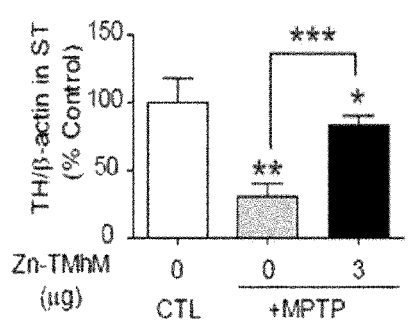
D 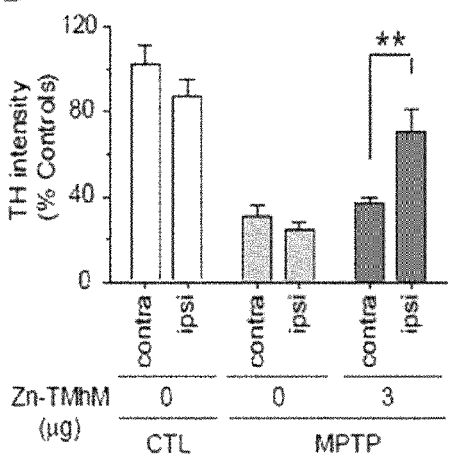

MITOCHONDRIA TARGETING PEPTIDE

CROSS-REFERENCE TO RELATED APPLICATION(S)

This application claims priority under 35 U.S.C. §119(e) to PCT Patent Application No. PCT/KR2013/007809 entitled "Mitochondrial Targeting Peptide," by Young Mi Kim, Young Cheol Kang and Yong Hee Kim, filed Aug. 30, 2013, and this application claims priority under 35 U.S.C. §119(b) to Korean Patent Application No. 10-2012-0096446 entitled "Mitochondrial Targeting Peptide," by Young Mi Kim, Young Cheol Kang and Yong Hee Kim, filed Aug. 31, 2012 of which are both assigned to the current assignee hereof and incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 3, 2015, is named 1214-P004_SL.txt and is 11,041 bytes in size.

TECHNICAL FIELD

The present invention relates to a mitochondria targeting peptide, a fusion protein in which the peptide is bound to the carboxyl terminus of a protein transduction domain, a fusion protein in which the peptide is bound to the carboxyl terminus of a protein transduction domain and an antioxidant is bound to the carboxyl terminus of the peptide, an antioxidant composition and a composition for preventing or treating Parkinson's disease including the fusion protein in which the antioxidant is bound thereto, a recombinant polynucleotide in which a polynucleotide encoding a protein transduction domain, a polynucleotide encoding the peptide, and a polynucleotide coding an antioxidant protein are sequentially bound, an expression vector including the polynucleotide, and a transformed host cell including the expression vector.

BACKGROUND ART

Mitochondria play a crucial role in numerous essential intracellular processes such as intracellular energetic metabolism, particular substance (e.g., fatty acids, etc.) metabolism, etc. Especially, mitochondria are directly involved in the formation and use of free radicals (FR) and reactive oxygen species (ROS). Due to such characteristics, in relation to extreme reactive moieties which may influence many intracellular processes in a living cell, mitochondria has been reported to play a crucial role in programmed cell death.

ROS is produced by a redox reaction in various organisms and can induce deterioration of edible oil and fat or oxidative damage on several biological substances (e.g., lipids, proteins, nucleic acids, and carbohydrates), consequently leading to cell damages through a number of steps (Yen G C. et al., J. Agric. Food Chem., 43, pp 27-32, 1995). An unsaturated fatty acid, which is a component of phospholipid membranes, initiates peroxidation by FR such as ROS in a chain reaction. Therefore, peroxidation by FR leads to overall cytotoxicity as well as increasing permeability of cell membranes, thus being involved in carcinogenesis by inducing aging and pathology of several aging-associated diseases. Radical activity greatly influences progression of various chronic diseases associated with oxidative stress such as atopic diseases, cancer, hypertension, myocardial infarction, arteriosclerosis, rheumatism, cataracts, Parkinson's disease, etc., (De Souza L C. et al., Bioorg. Med. Chem. Lett., 14, pp 5859-5861, 2004), and can act as a factor for weakening immune functions (Pike J. et al., Int. J. Vitam. Nutr. Res., 65, pp 117-120, 1995). Especially, oxidative stress induced by hypergenesis of ROS serves as a cause of many degenerative diseases including neurodegenerative disorders. Mitochondria are where ROS is mainly generated and are intracellular organelles most susceptible to damages by ROS. Therefore, a number of diseases in association with FR and ROS hypergenesis are known to be related to dysfunction of mitochondria.

Thus, for the purpose of recovering mitochondrial functions, carriers and/or drugs targeting mitochondria have been proposed. By repeatedly accumulating a substance in a target compartment of a cell, such approach can allow reaching an effective concentration of the substance. Thus, it has advantages of increased application efficiencies, reduced overall dosages, and reduced possibilities and intensities of side effects.

Currently, a very limited number of mitochondria-targeting biological active substances are known. Examples thereof are mitovitamin E (MitoVitE) or superoxide dismutase and glutathione peroxidase mimetics associated with triphenyl phosphonium, which are disclosed in European Patent 1 534 720.

DETAILED DESCRIPTION

Technical Problem

Thus, the present inventors produced a novel mitochondria targeting sequence while conducting research on a method for effectively transporting substances which are difficult to pass through cellular and mitochondrial membrane structures. They completed the present invention upon confirming that when the sequence is bound to a protein transduction domain and/or an antioxidant, the antioxidant is effectively transported into mitochondria.

Technical Solution

An objective of the present invention is to provide a mitochondria targeting peptide represented by an amino acid sequence of Formula 1 as follows:

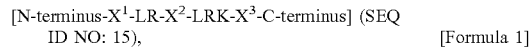

wherein
$X^1$ is absent or a hydrophobic amino acid;
$X^2$ is two identical hydrophobic amino acids; and
$X^3$ is GPRLSRL (SEQ ID NO: 16), GPRLSRM (SEQ ID NO: 17), AA or AAL.

Another objective of the present invention is to provide a fusion protein in which the peptide is bound to the carboxyl terminus of a protein transduction domain.

Another objective of the present invention is to provide a fusion protein in which the peptide is bound to the carboxyl terminus of a protein transduction domain and an antioxidant is bound to the carboxyl terminus of the peptide.

Another objective of the present invention is to provide an antioxidant composition which includes a fusion protein to which the antioxidant is bound, or a composition for preventing or treating Parkinson's disease.

Another objective of the present invention is to provide a recombinant polynucleotide in which a polynucleotide encoding a protein transduction domain, a polynucleotide encoding a peptide, and a polynucleotide encoding an antioxidant protein are sequentially bound thereto, an expression vector including the polynucleotide, and a host cell transformed by the expression vector.

Another objective of the present invention is to provide a method for preventing or treating Parkinson's disease which includes administering a pharmaceutical composition for preventing or treating Parkinson's disease, which includes a fusion protein to which the antioxidant is bound.

Another objective of the present invention is to provide a use of a fusion protein to which the antioxidant is bound for producing a pharmaceutical drug for preventing or treating Parkinson's disease.

Advantageous Effects

The mitochondria targeting peptide according to the present invention targets mitochondria with high efficiency not only when the peptide exists alone but also when the peptide is bound to a protein transduction domain and/or to an antioxidant. Further, the peptide has a small size and is thus a very suitable targeting carrier. The peptide becomes processed when introduced into mitochondria, and thus stably delivers the drug carried by the peptide.

DESCRIPTIONS OF DRAWINGS

FIG. 2 shows (A) a drawing representing a processing site of TAT-MTS (SEQ ID NO: 24); (B) a TAT-MTS structure predicted using a COOT program; and (C) a schematic diagram representing amphiphile of TAT-MTS using a helical wheel projection, according to an embodiment of the present invention (SEQ ID NO: 25).

FIG. 3 shows (A) results from Western blot analysis of lysates of cells and mitochondria after TMhM treatment; and (B) confocal laser scanning microscopy results after immunocytochemcial staining, according to an embodiment of the present invention. FIGS. 3A and 3B disclose "6×His" as SEQ ID NO: 19.

Figure 4:
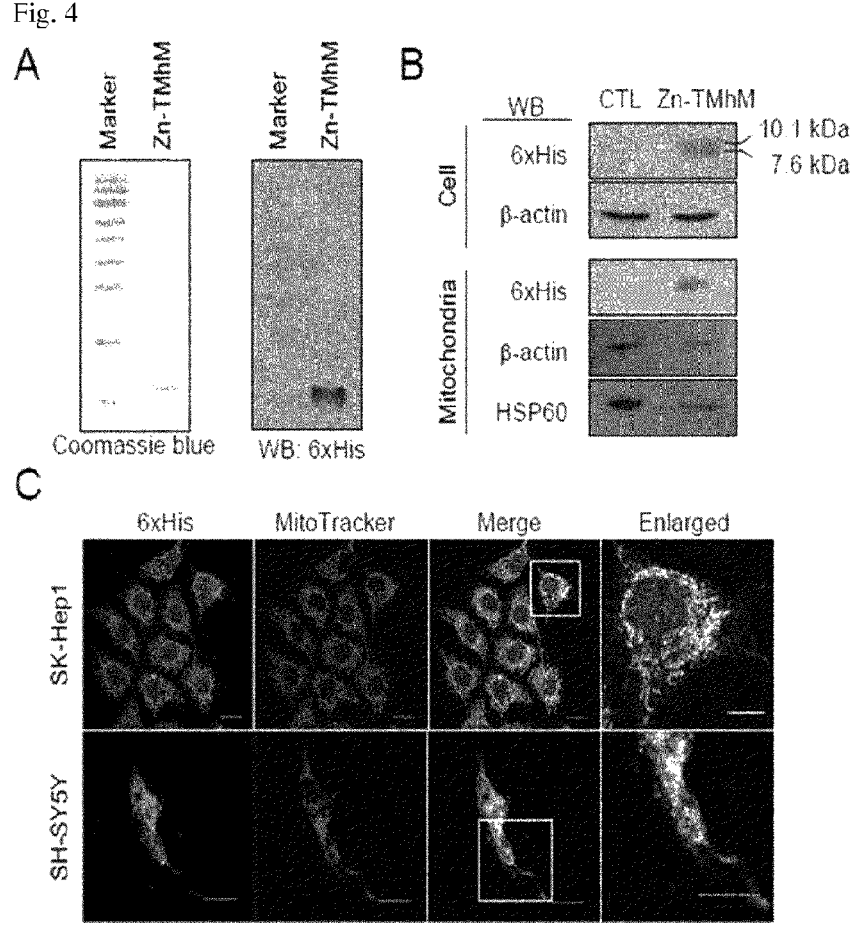

FIG. 4 shows (A) results from Coomassie staining (left) and Western blot analysis (right) after Zn-TMhM treatment; (B) results from Western blot analysis of lysates of cells and mitochondria after Zn-TMhM treatment; and (C) confocal laser scanning microscopy results after immunocytochemcial staining, according to an embodiment of the present invention. FIGS. 4B and 4C disclose "6×His" as SEQ ID NO: 19.

Figure 5:
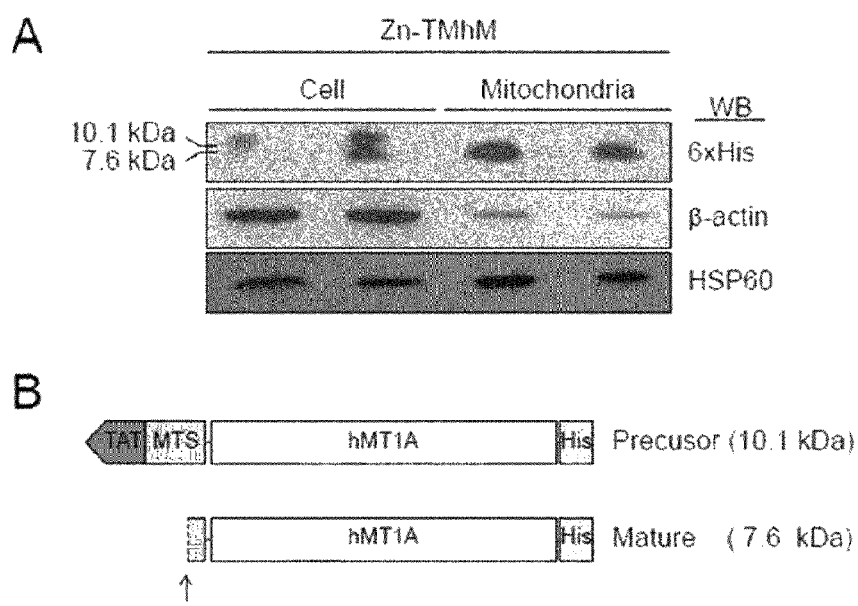

FIG. 5 shows (A) results from Western blot analysis which confirmed the processing of Zn-TMhM; and (B) a processing structure, according to an embodiment of the present invention. FIG. 5A discloses "6×His" as SEQ ID NO: 19.

Figure 6:
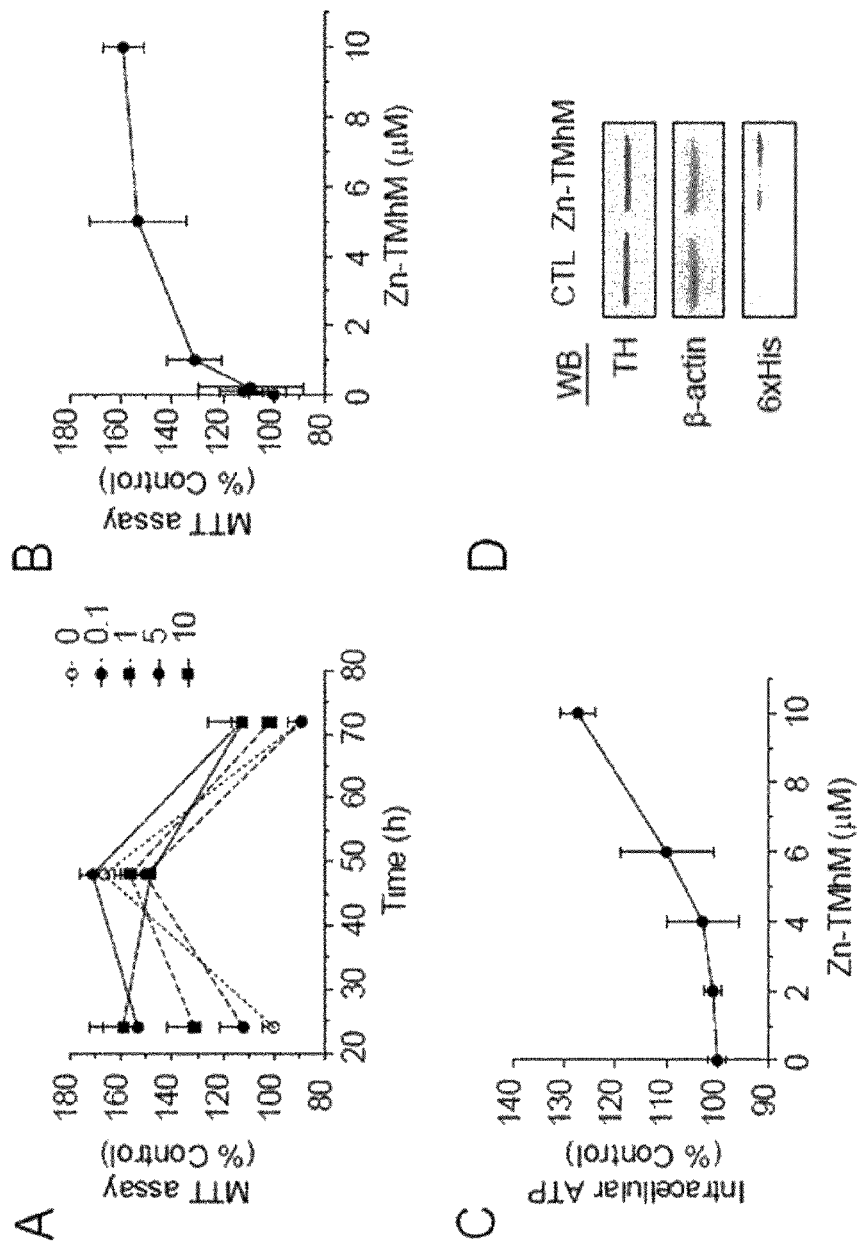

FIG. 6 shows whether Zn-TMhM exhibits cytotoxicity via (A and B) effects on cell viability; (C) ATP amount; and (D) results from Western blot analysis which confirmed effects on tyrosine hydroxylase (TH), according to an embodiment of the present invention. FIG. 6D discloses "6×His" as SEQ ID NO: 19.

Figure 7:
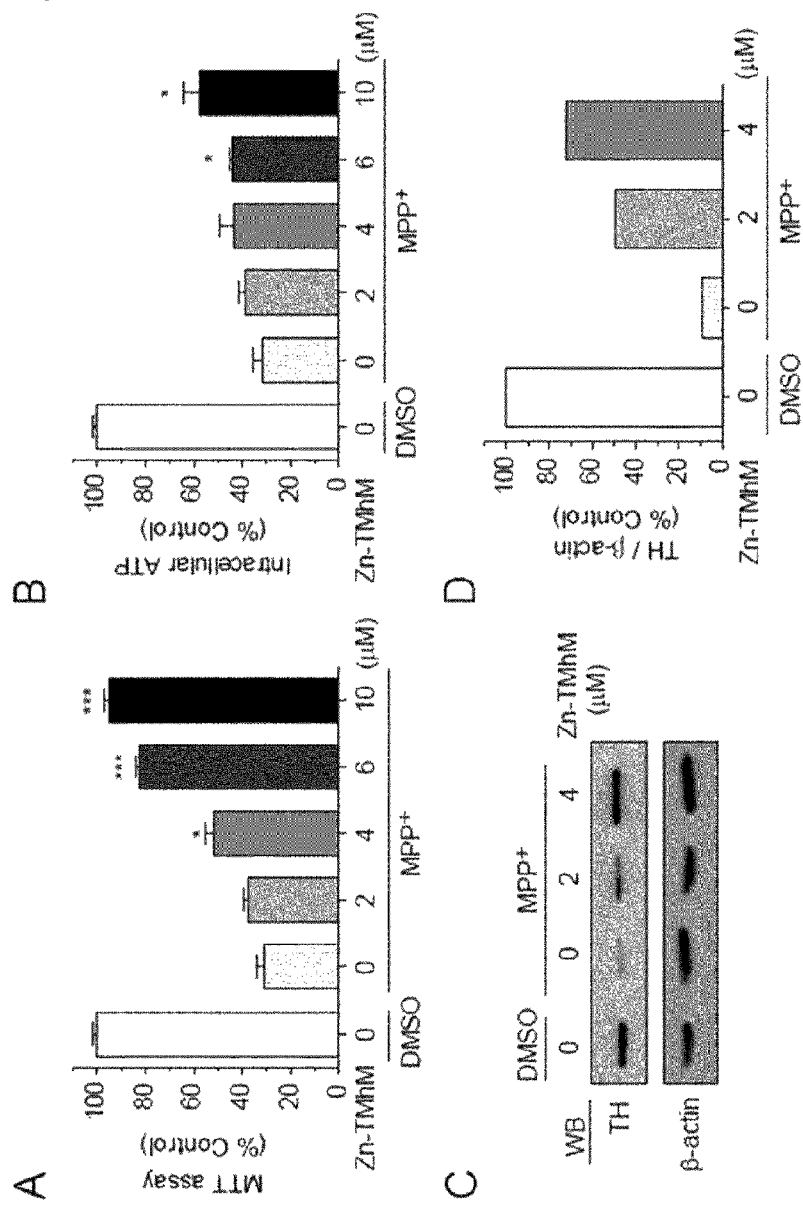

FIG. 7 shows (A) MTT assay results; (B) ATP amount; (C) Western blot analysis; and (D) effects on tyrosine hydroxylase (TH) after Zn-TMhM treatment in MPP⁺-induced Parkinson's cell models, according to an embodiment of the present invention.

Figure 8:
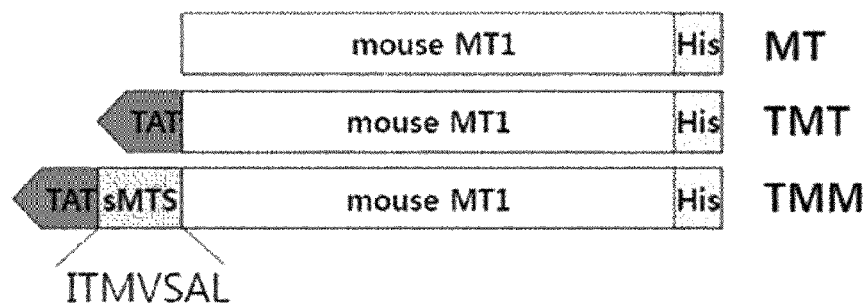

FIG. 8 shows results from Western blot analysis which confirmed mitochondria targeting effects in mice, according to an embodiment of the present invention. FIG. 8 discloses SEQ ID NO: 20.

Figure 9:
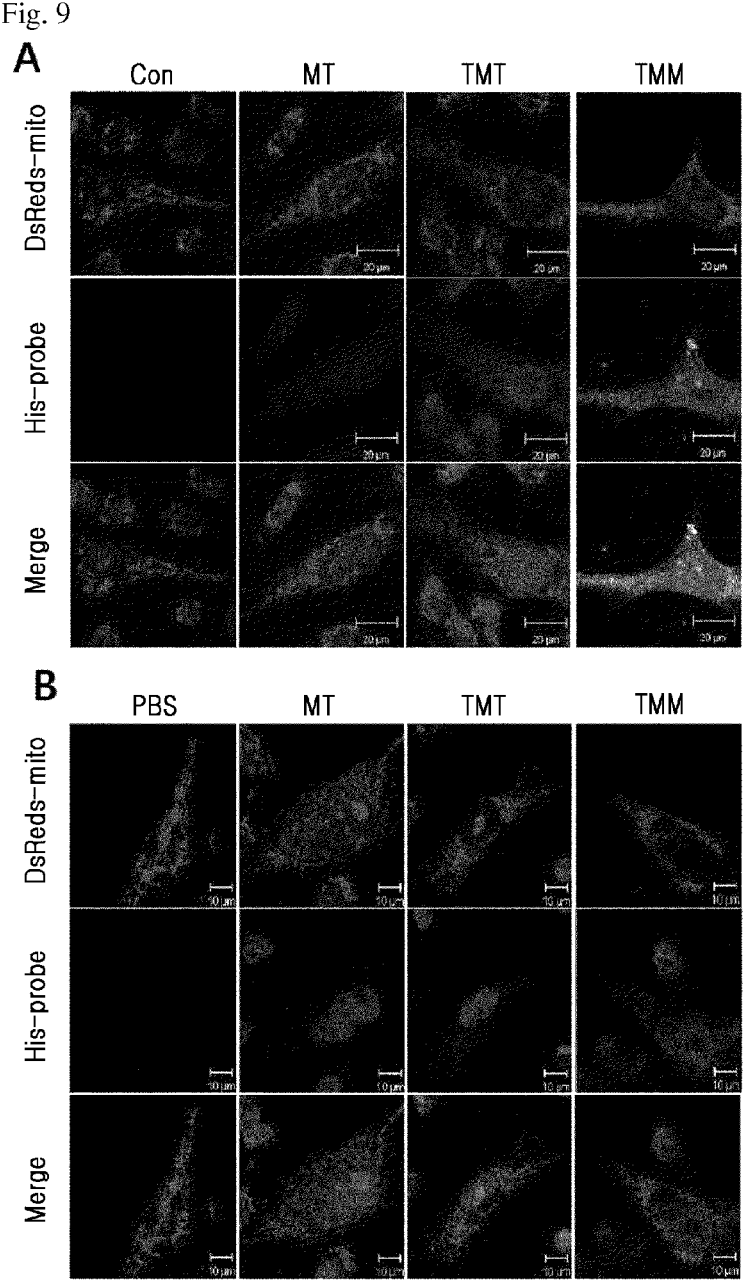

FIG. 9 shows results from an assay which confirmed ROS effects of a mitochondria targeting sequence, according to an embodiment of the present invention.

Figure 10:
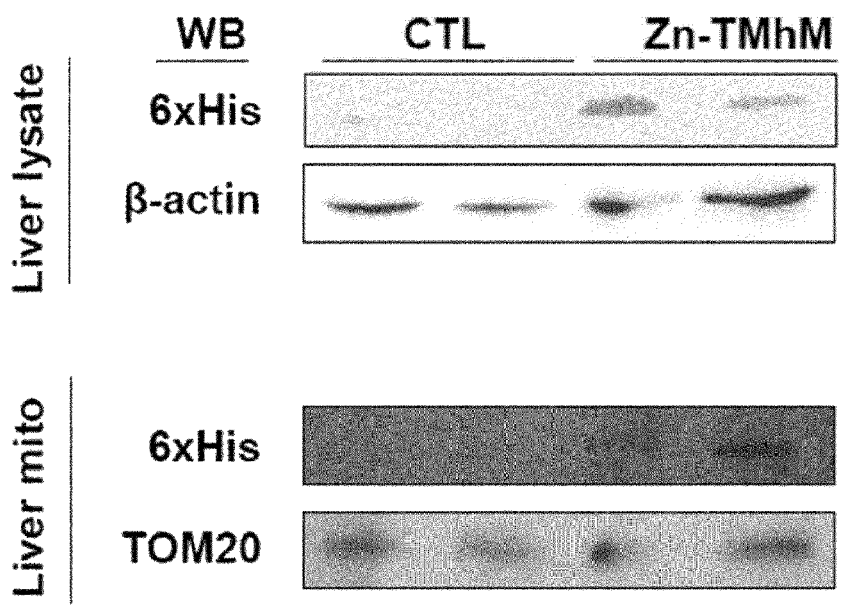

FIG. 10 is a schematic drawing of comparative sequences, according to an embodiment of the present invention. FIG. 10 discloses "6×His" as SEQ ID NO: 19.

Figure 11:
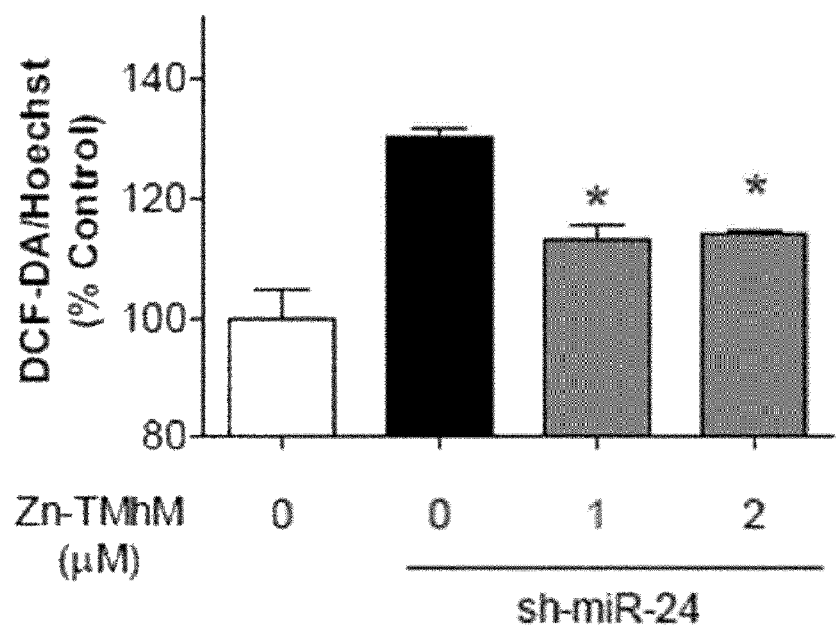

FIG. 11 shows confocal laser scanning microscope results of comparative sequence expressions (localizations) according to an embodiment of the present invention.

Figure 12:
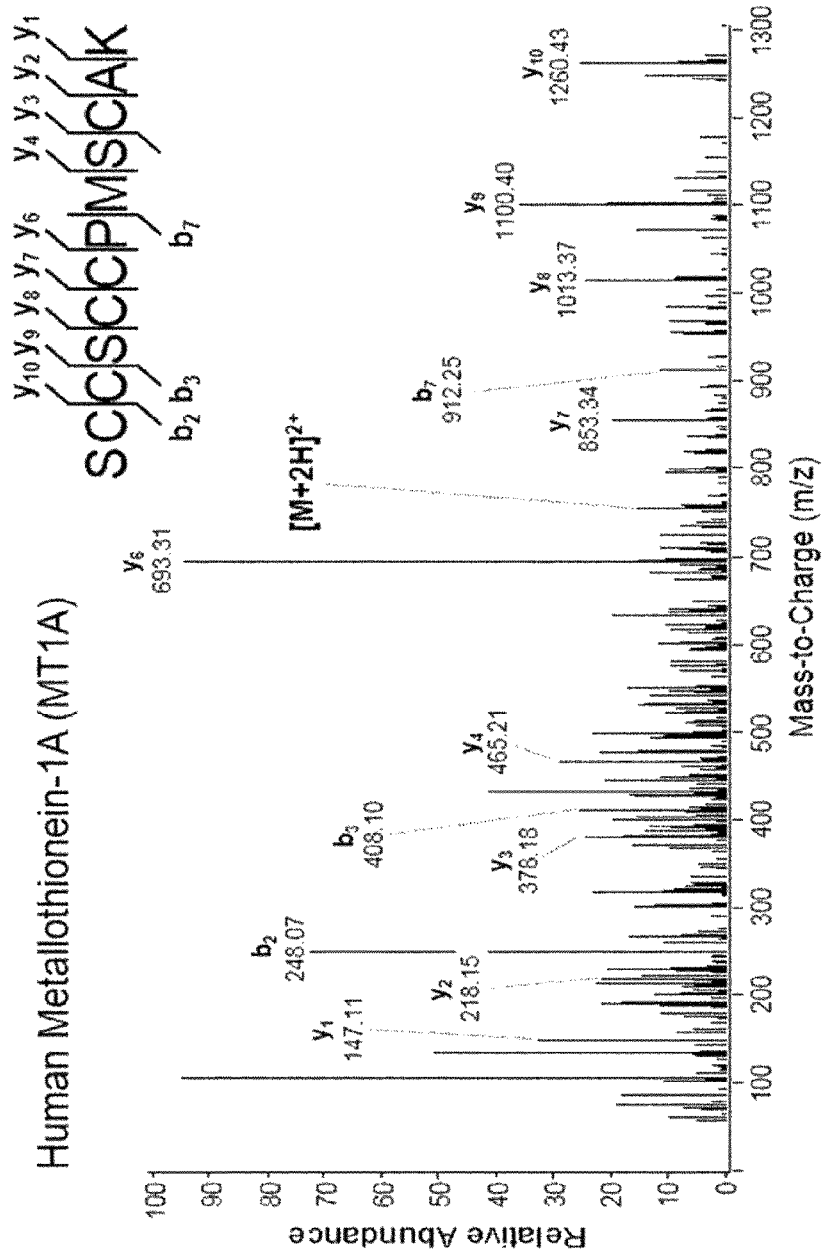

FIG. 12 is a drawing which confirmed that Zn-TMhM used in the present invention is human MT1A by examining a sequence via Maldi-TOF/Ms/Ms. FIG. 12 discloses SEQ ID NO: 26.

Figure 13:
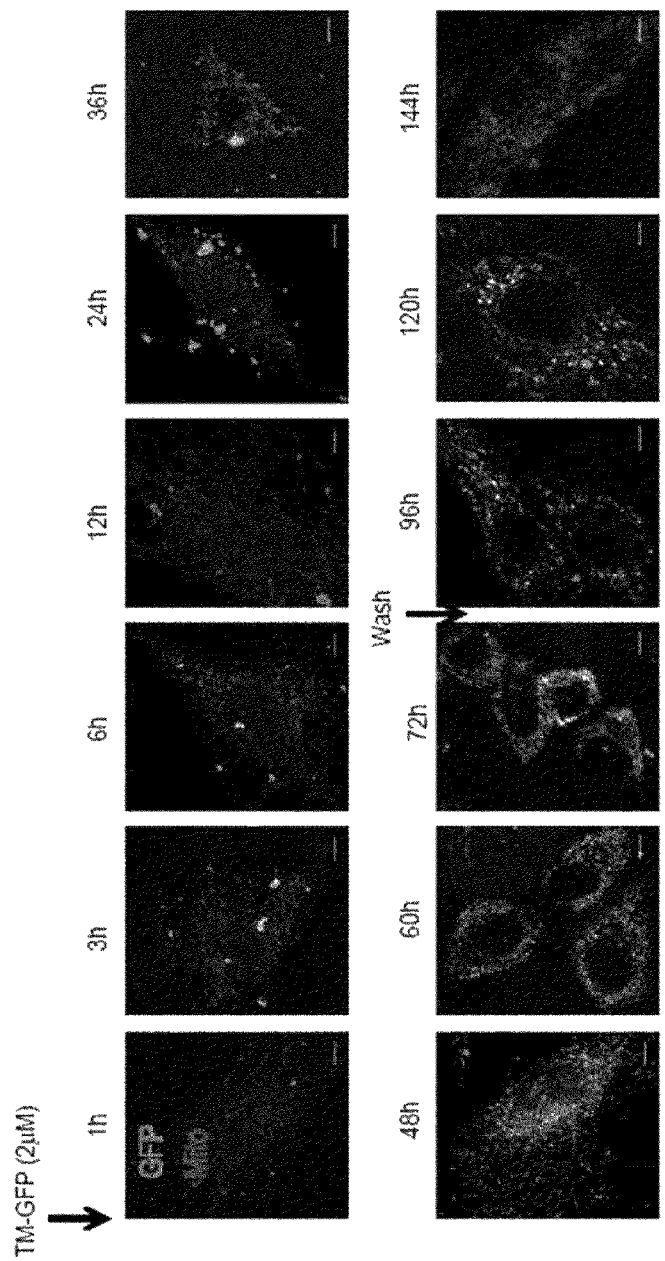

FIG. 13 shows images which confirmed time duration wherein TAT-MTS activity is maintained in mitochondria.

Figure 14:
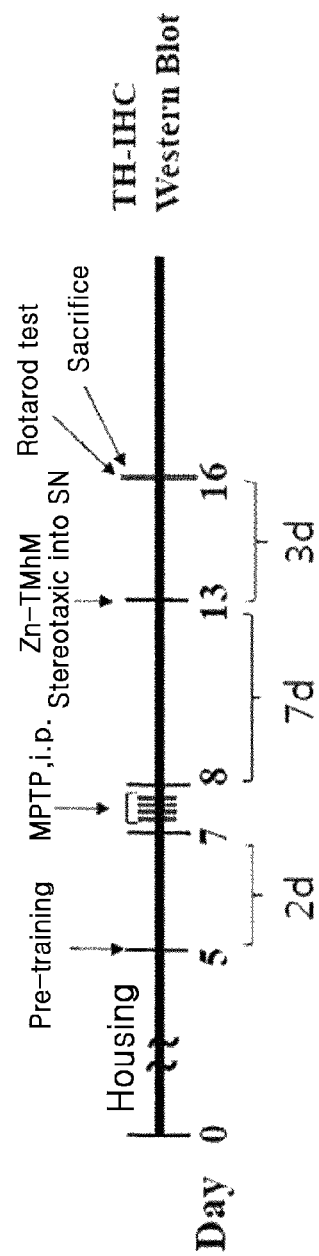

FIG. 14 is a schematic diagram of model production and experimental conditions organized in a time series order to confirm therapeutic effects of Zn-TMhM in MPTP-induced Parkinson's mouse models.

FIG. 15 shows graphs which confirmed therapeutic effects of Zn-TMhM in MPTP-induced Parkinson's animal models via (A) motor abilities on a rotarod test ($p<0.01$); and (B to D) signal intensity or a number of TH-positive neurons (dopaminergic neurons) (*$p<0.05$, ***$p<0.001$).

BEST MODE

In an aspect of achieving the objectives, the present invention relates to a novel mitochondria targeting peptide represented by an amino acid sequence of Formula 1 below:

[N-terminus-$X^1$-LR-$X^2$-LRK-$X^3$-C-terminus](SEQ ID NO: 15),     [Formula 1]

wherein $X^1$ is absent or a hydrophobic amino acid;
$X^2$ is two identical hydrophobic amino acids; and
$X^3$ is GPRLSRL (SEQ ID NO: 16), GPRLSRM (SEQ ID NO: 17), AA or AAL.

The amino acid sequences used in the present invention are abbreviated according to the nomenclature of IUPAC-IUB as follows:

| Alanine | A | Arginine | R |
| --- | --- | --- | --- |
| Asparagine | N | Aspartic acid | D |
| Cysteine | C | Glutamic acid | E |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |
| Glutamine | Q | Glycine | G |

As used herein, the term "peptide" refers to a polymer consisting of amino acids linked by amide bonds (peptide bonds).

A peptide according to the present invention exhibits an effective mitochondria targeting activity by including a fragment which contains a sequence comprising a hydrophobic amino acid at the N-terminus and C-terminus. Here, a hydrophobic amino acid can be any hydrophobic amino acid, such as methionine, alanine, valine or leucine, although not limited thereto.

Preferably in Formula 1, $X^1$ may be absent, or methionine, alanine, or leucine, and $X^2$ may be alanine or leucine. More preferably, $X^1$ may be leucine and $X^2$ may be alanine.

A novel peptide of Formula 1 according to the present invention may be representatively any one of the following sequences 1 to 10:

```
SEQ ID NO: 1:
LLRAALRKAA;

SEQ ID NO: 2:
LLRAALRKAAL;

SEQ ID NO: 3:
LLRLLLRKAA;

SEQ ID NO: 4:
LLRLLLRKAAL;

SEQ ID NO: 5:
MLRAALRKGPRLSRL;

SEQ ID NO: 6:
LRAALRKGPRLSRL;

SEQ ID NO: 7:
ALRAALRKGPRLSRL;

SEQ ID NO: 8:
MLRAALRKGPRLSRM;

SEQ ID NO: 9:
LLRAALRKGPRLSRM;
and

SEQ ID NO: 10:
ALRAALRKGPRLSRM.
```

According to an exemplary embodiment of the present invention, a mitochondria targeting peptide according to the present invention has an alpha-helical structure and is amphiphilic (Example 2).

The peptide of the present invention may include an additional amino acid sequence designed for a particular purpose of increasing stability of a targeting sequence, a tag, a labeled moiety, a half-life, or a peptide. Additionally, the peptide of the present invention may be linked to coupling partners such as effectors, drugs, prodrugs, toxins, peptides, carrier molecules, etc.

The peptide of the present invention may be obtained by various methods well known in the art. In particular, it may be produced by genetic recombination and protein expression system, an in vitro synthesis via chemical synthesis such as peptide synthesis and cell-free protein synthesis.

The peptide of the present invention may be produced in the form of a pharmaceutically acceptable salt. In particular, a salt may be formed by adding an acid. For example, a salt may be formed by adding a mineral acid (e.g., hydrochloric acid, hydrobromic acid, phosphoric acid, nitric acid, sulfuric acid, etc.), an organic carboxylic acid (e.g., acetic acid, haloacetic acid such as trifluoroacetic acid, propionic acid, maleic acid, succinic acid, malic acid, citric acid, tartaric acid, and salicylic acid), and an organic sulfonic acid (e.g., methanesulfonic acid, and p-toluenesulfonic acid) containing sulfonic acid sugar esters such as an acidic sugar (e.g., glucuronic acid, galacturonic acid, gluconic acid, and ascorbic acid), an acidic polysaccharide (e.g., hyaluronic acid, chondroitin sulfate, and arginine acid), and chondroitin sulfate.

A peptide of the present invention may be connected to an internalizing sequence, a protein transduction domain, or a cell membrane-penetrating protein so that it can effectively enter into a cell.

Accordingly, in another aspect, the present invention relates to a fusion protein in which a peptide of Formula 1 is bound to the carboxyl terminus of a protein transduction domain.

The protein transduction domain and the peptide of Formula 1 may be fused chemically or biologically by using techniques well known in the art without limitations.

As used herein, the term, "protein transduction domains" refers to polypeptides, polynucleotides, carbohydrates, or organic/inorganic compounds which facilitate passing through lipid bilayers, micelles, cell membranes, organelle membranes, and vesicle membranes. The protein transduction domain includes a small portion of a protein which can pass through a cell membrane by a receptor-independent mechanism. By bonding with another molecule, a protein transduction domain can act to facilitate transporting a particular molecule from the extracellular space to the intracellular space or from the cytosol to the inside of an organelle.

The protein transduction domain according to the present invention may be one or more peptides from the group comprising a transactivator of transcription (TAT) protein of HIV-1 virus, polyarginine, penetratin, a transcription regulatory protein of VP22 which is a structural protein of HSV-1, PEP-1 peptide, and PEP-2 peptide, although not limited thereto. Preferably, the protein transduction domain is a polypeptide of the following SEQ ID NO: 11 or 12:

SEQ ID NO: 11: YGRKKRRQRRR
SEQ ID NO: 12: YARAAARQARA.

SEQ ID NO: 11 is a TAT protein transduction domain of HIV consisting of 11 amino acid sequences. Because its molecular weight is low, it is appropriate for fusion with a protein that needs to be transported to the intracellular space.

A fusion protein according to the present invention exhibits targeting ability to localize inside mitochondria as well as permeating ability, and can be effectively used as a cargo molecule or a drug delivery system.

Another aspect of the present invention relates to fusion protein in which a peptide of Formula 1 is bound to the carboxyl terminus of a protein transduction domain of the present invention and an antioxidant additionally is bound to the carboxyl terminus of the peptide.

According to a specific embodiment of the present invention, a fusion protein consisting of a mitochondria targeting sequence and SEQ NO: 11 targeted mitochondria with a high score. Also, even when GFP and hMT1A are additionally bound, mitochondria is effectively targeted (Example 1).

Further, according to a specific embodiment of the present invention, a fusion protein consisting of a mitochondria targeting sequence, SEQ NO: 11, and hTM1A are shown to be transported to mitochondria via a Western blot and immunocytochemical staining (Examples 6 and 7). Also, a long-term activity maintained in mitochondria was confirmed (FIG. 13).

In addition, according to a specific embodiment of the present invention, mitochondria targeting probability was predicted for a mitochondria targeting sequence according to the present invention which is bound not only to hMT1A, but also to intracellular antioxidant protein SOD1, catalase, EPX, GPX, and PARK2 or LRRK2 which are PD-related proteins, with TAT-MTS. Results showed that all proteins are targeted to mitochondria at almost 100% probability (Example 9).

Therefore, a novel peptide fusion protein binding to a protein transduction domain according to the present invention is able to bind to compounds, drugs, antibodies, and other substances to be transported, and transport them into mitochondria. Substances which bind to the fusion protein are not limited to a certain kind, as long as they are able to bind to the fusion protein.

Another aspect of the present invention relates to an antioxidant composition which includes a fusion protein consisting of a novel mitochondria targeting peptide, a protein transduction domain, and an oxidant.

Since ROS is mostly produced in mitochondria, when a fusion protein according to the present invention, to which an antioxidant is bound, is transported into mitochondria, there is an advantage of maximizing effects of the antioxidant.

The antioxidant according to the present invention may be, for example, SOD1, catalase, EPX, GPX, PARK2, LRRK2, or metallothionein. Preferably, the antioxidant according to the present invention is metallothionein. More preferably, the metallothionein is human metallothionein.

As used herein, the term "metallothionein (MT)" refers to a cysteine-rich low molecule (3.5~14 kDa) consisting of 61 amino acids in a structure repeating cysteine-X-cysteine, cysteine-XX-cysteine, and cysteine-cysteine. Metallothionein refers to a protein which includes 20 cysteine residues that bind to a divalent metal ion. Metallothionein is overexpressed in stressful conditions such as heavy metals, starvation, heat, or infections. Metallothionein has been considered as an important biophylaxic means and is known to act in defense mechanism against oxidative stress. Commonly, biological defense against oxidative damage by ROS consists of proteins eliminating ROS, molecules isolating metal ions, and enzymes restoring damaged cellular components.

In addition, it has been recently reported that metallothionein can protect cells and tissues from diabetes and diabetic complications in vitro and in vivo because of its anti-apoptotic and antioxidant capacities (K. G. Danielson et al., Proc Natl Acad Sci USA. 79 (1982) 2301-04). It has been reported that when metallothionein is overexpressed in MT null diabetic mice, diabetic cardiomyopathy is reduced, and impaired ischemic heart contraction is alleviated (A. Liang et al., Diabetes. 51 (2002) 174-181). Zinc also induces expression of metallothionein and protects mice from diabetic damages caused by hyperglycemia and progressive damages in beta cells of type 2 diabetes. It is also known that zinc-metallothionein is capable of blocking hydroxyl radicals in vitro and in vivo (C. G. Taylor et al., Biometals. 18 (2005) 305-312).

According to an exemplary embodiment of the present invention, when a fusion protein including metallothionein of the present invention was administered to cells, cell viability was maintained, ATP production was increased, and tyrosine hydroxylase activity was recovered (Example 10). Additionally, when a fusion protein including human metallothionein was administered to Parkinson's cell models, mitochondrial activity was recovered (Example 11, FIGS. 7A and 7B).

In addition, according to an exemplary embodiment of the present invention, when a fusion protein including an antioxidant of the present invention is administered to mice, target-transport to mitochondria in liver cells (Example 12), and effects of eliminating ROS (Example 13) were confirmed.

In addition, according to a specific embodiment of the present invention, when a fusion protein including an antioxidant according to the present invention is administered to mice of MPTP-derived Parkinson's animal models, mice recovered to the normal level in behavioral perspectives. Also, brain tissue analysis showed that dopaminergic neurons were recovered, thus confirming possible applications in treating Parkinson's disease by restoring cell damages, as well as preventing Parkinson's disease by preventing cell damages (FIG. 15, Example 14).

Therefore, a fusion protein including an antioxidant according to the present invention may be used as an agent preventing or treating any disorders or diseases induced by oxidative stress. Especially, it may be used effectively for brain disorders such as Parkinson's disease and diabetic diseases described above.

In another aspect, the present invention relates to a method for preventing or treating diseases induced by stress (e.g., brain disorders such as Parkinson's disease, diabetic diseases, etc.) by administering a pharmaceutical composition including a fusion protein including the antioxidant for preventing or treating diseases induced by oxidative stress to humans or mammals in need.

As used herein, the term "subject" refers to mammals which include mice, cattle, humans, etc., although not limited thereto.

In addition, a pharmaceutical composition of the present invention may be administered via various routes. Administration according to the present invention refers to introducing a prescribed substance into a patient via any appropriate method, and a route of administration of the conjugate may be any common methods as long as a drug reaches a target tissue. Particularly, the pharmaceutical composition may be administered via intraperitoneal administration, intravenous administration, intramuscular administration, subcutaneous administration, intradermal administration, oral administration, topical administration, intranasal administration, intrapulmonary administration, and intrarectal administration, but is not limited thereto. However, because a peptide is digested when administered orally, it is preferred that a composition for oral administration is formulated to coat an active substance or to be protected against degradation in stomach. Preferably, it may be administered in the form of injections. Additionally, a pharmaceutical composition may be administered by any device which can transport active substances to target cells.

Although a preferred dosage of a fusion protein including the antioxidant according to the present invention differs depending on conditions and weight of mammals including humans, severity of a disease, drug type, administration route, and duration, it may be appropriately selected by one of ordinary skill in the art. Further, any method of administration may be predicted. For example, it may be administered via oral, rectal, intravenous, subcutaneous, intrauterine epidural, or cerebrovascular injections, although not limited thereto.

A fusion protein with or without an antioxidant according to the present invention may have a poly-His domain bound to the carboxyl terminus.

A fusion protein including an antioxidant of the present invention has a feature of stably delivering drugs after transportation into mitochondria and processing.

According to an exemplary embodiment of the present invention, the fusion protein according to the present invention was observed as a mature form of 7.6 kDa inside mitochondria after being processed by a matrix metalprotease, a mitochondrial matrix signal peptide processing enzyme. After being processed, the present invention was observed to become hMT1A, which includes His-tag and amino acid residues (AAGKL) (SEQ ID NO: 18) (Example 8).

In another aspect, the present invention relates to a recombinant polynucleotide in which a polynucleotide encoding a protein transduction domain, a polynucleotide encoding the mitochondria targeting peptide, and a polynucleotide encoding an antioxidant protein are sequentially bound. The recombinant polynucleotide may be produced by conventional methods using known sequences encoding a novel polynucleotide encoding a protein transduction domain, a mitochondria targeting peptide, and an antioxidant protein. Especially, a recombinant polynucleotide of the present invention may include sequences of nucleic acids of SEQ ID NO: 13 or 14.

In another aspect, the present invention relates to an expression vector including the polynucleotide.

As used herein, the term "expression vector" refers to a recombinant vector capable of expressing a target peptide in an appropriate host cell and to a genetic construct which includes essential regulatory factors coupled to express genetic inserts. An expression vector of the present invention includes expression regulatory factors such as a promoter, an operator, and a start codon, which are generally included in expression vectors. A start codon and a stop codon are considered to be parts of nucleotide sequences encoding polypeptides, and are required to show activities when genetic constructs are introduced and be in frame with a coding sequence. A promoter of a vector may be constitutive or inductive.

In addition, in order to facilitate separation of a protein from a cell culture, a signal sequence for emitting fusion polypeptide may be included. Specific initiation signals may also be required for effective translation of inserted nucleic acid sequences. These signals include ATG start codon and adjacent sequences. In some cases, external translation regulatory signals capable of including ATG start codon should be provided. The external translation regulatory signals and start codons may come from various natural or synthetic sources. Expression efficiency may be increased by introducing appropriate transcription or translation enhancers.

As expression vectors, any conventional expression vectors may be used. For example, plasmid DNA, phage DNA, etc., may be used. Specific examples of plasmid DNA include commercial plasmids such as pUC18 and pIDT-SAMART-AMP. Other examples of plasmids, which may be used in the present invention are, *E. coli*-derived plasmids (pYG601BR322, pBR325, pUC118 and pUC119), *Bacillus subtilis*-derived plasmids (pUB110 and pTP5), and yeast-derived plasmids (YEp13, YEp24, and YCp50). Specific examples of phage DNA are λ-phage (Charon4A, Charon21A, EMBL3, EMBL4, λgt10, λgt11, and λZAP). Further, animal viruses such as retrovirus, adenovirus, or vaccinia virus, or insect viruses such as baculovirus may be used. Since such expression vectors exhibit different protein expression amounts, formula, etc., depending on host cells, appropriate host cells should be selected.

In another aspect, the present invention relates to a host cell transformed by the expression vector.

As used herein, the term "transformation" refers to a stable genetic alteration in which the polynucleotide fragment is moved into the genome of a host cell for expressing targeted peptides.

A fusion protein including an antioxidant according to the present invention may be prepared by methods including:
(1) a step of transforming a host cell by a recombinant expression vector including a recombinant polynucleotide in which a polynucleotide encoding a protein transduction domain represented by an amino acid sequence of SEQ ID NO: 11 or 12 is bound to the 5' terminus of a polynucleotide encoding a mitochondria targeting sequence represented by an amino acid sequence selected from the group consisting of SEQ ID. NOS: 1 to 10, and a polynucleotide encoding an antioxidant protein is bound to the 3' terminus of a polynucleotide encoding a mitochondria targeting sequence represented by the amino acid selected from the group consisting of SEQ ID NOS: 1 to 10;
(2) a step of expressing an antioxidant fusion protein by culturing the transformed host cell; and
(3) a step of purifying an expressed antioxidant fusion protein.

The transformation of the present invention may be performed by any transformation methods and may be easily performed according to conventional methods in the art. Generally, transformation methods include $CaCl_2$ precipitation, Hananhan method of which efficiency is increased by using a reducing agent, dimethyl sulfoxide (DMSO) in $CaCl_2$ method, electroporation, calcium phosphate precipitation, protoplast fusion, agitation using silicon carbide fiber, agrobacteria-mediated transformation, transformation using PEG, dextran sulfate, lipofectamine, drying/inhibition-mediated transformation, etc.

The host cell is not limited to a certain kind, as long as it expresses a peptide of the present invention, and preferably may be a microorganism. Specific examples of a microorganism that may be used in the present invention are bacteria belonging to the genus *Escherichia* such as *E. coli*, bacteria belonging to the genus *Bacillus* such as *Bacillus subtilis*, bacteria belonging to the genus *Pseudomonas* such as *Pseudomonas putida*, and yeasts such as *Schizosaccharomyces pombe* and *Saccharomyces cerevisiae*, animal cells and insect cells.

In another aspect, the present invention relates to the use of a fusion protein to which the antioxidant is bound in producing a pharmaceutical drug for preventing or treating Parkinson's disease.

MODE FOR INVENTION

Hereinafter, the present invention will be described in more detail with reference to Examples, However, these Examples are for illustrative purposes only, and the invention is not intended to be limited by these Examples.

Example 1

Production of a Novel Mitochondria Targeting Sequence (MTS)

In order to test mitochondria targeting probabilities, (TAT which is a protein transduction domain with cell membrane permeability), (TAT+mitochondria targeting sequence), and (TAT+mitochondria targeting sequence+protein to be targeted) are grouped and produced respectively. Hereinafter, a mitochondria targeting sequence is abbreviated as MTS.

MTS according to the present invention is artificially produced, and the respective mitochondria targeting probabilities thereof are virtually predicted using a program 'MitoProt II.' Specifically, as a mitochondria sequence according to the present invention, aMTS consisting of SEQ ID NO: 2 (LLRAALRKAAL) is used. As a comparison, sequences derived from malate dehydrogenase (mMDH), succinate dehydrogenase subunit alpha (SDHA), and mitochondria aldehyde dehydrogenase (ALDH2) were used. By binding TAT to each of the sequences, virtual TAT-MTS was produced, and mitochondria targeting probabilities were calculated and shown in Table 1B.

Figure 1:
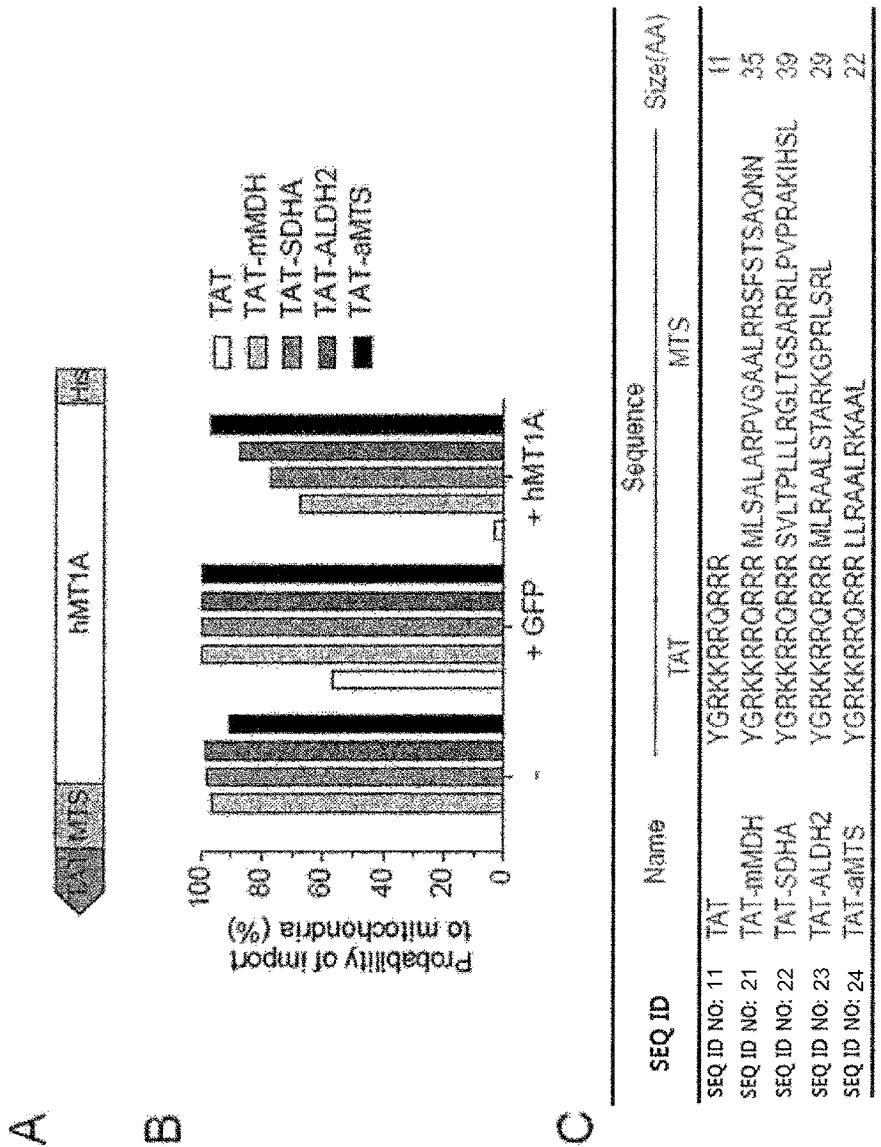
FIG. 1 shows (A) an in silico design of a mitochondria targeting sequence; (B) a graph of a predicted targeting probability of various kinds of mitochondria targeting sequences to which a TAT sequence is bound using MitoProt II; and (C) a table representing each sequence and size, according to an embodiment of the present invention (SEQ ID NOS 11 and 21-24, respectively, in order of appearance).

In addition, in order to verify whether mitochondria targeting ability remains intact not only with TAT-MTS, but also with a protein bound, green fluorescence proteins (GFP) and human metallothionein 1A (hMT1A) proteins were additionally bound to the produced sequences. The binding structure was produced corresponding to the structure of TAT-MTS-hMT1A as shown in FIG. 1A. Mitochondria targeting probabilities of TAT-proteins and TAT-MTS-proteins were calculated using MitoProt II and the results are shown in Table 1B.

As shown in Table 1B, TAT-mMDH, TAT-SDHA, TAT-ALDH2, and TAT-aMTS to which a protein was not bound targeted mitochondria at a probability close to 100%. When GFP was bound, the mitochondria targeting probability of TAT was substantially decreased to 56.8%, but when TAT-ALDH and MTS were bound together, TAT was expected to target mitochondria over 98%. When hMT1A was bound, the mitochondria targeting probability was 67.7% for TAT-mMDH-hMT1A. 77.1% for TAT-SDHA-hMT1A, and 87.6% for TAT-ALDH2-hMT1A, thus confirming a decreased mitochondria activity. On the other hand, TAT-aMTS-hMT1A showed 100% mitochondria targeting probability, thus confirming an effective mitochondria targeting activity even when a transduction protein was bound instead of GFP.

A comparison of the sequences and sizes of TAT, TAT-mMDH, TAT-SDHA, and TAT-ALDH2 are shown in FIG. 1C. As shown in FIG. 1C, LLRAALRKAAL of SEQ ID NO: 2 which showed a 97% targeting score consists of 11 amino acids and has a significantly smaller size compared to those of mMDH, SDHA, or ALDH2.

Example 2

Prediction on Mitochondria Targeting Sequence (MTS) Structure

In order to verify if TAT-MTS is transported to mitochondria, a secondary structure of a TAT-MTS peptide was predicted and represented in FIG. 2.

Results from a COOT program showed that the TAT-MTS peptide exhibits an alpha-helical structure (FIG. 2B). Further, a helical wheel projection showed that TAT-MTS is amphiphilic (FIG. 2C). Also, MitoProt II program predicted that a processing site exists between TAT-MTS and hMT1A (FIG. 2A). The processing site is where noted by an underbar and corresponds to a processing site, which is cut when TAT-MTS-hMT1A is transported into mitochondria. From the results of the structure analysis, the present inventors determined that TAT-MTS peptides have a sufficient ability to transport MT1A to mitochondria.

Example 3

Cell Culture

SK-Hep1 cells (human hepatocellular carcinoma cells) were cultured in high glucose (4.5 g/L) Dulbecco's Modified Eagle's Medium (DMEM) supplemented with 10% fetal bovine serum (FBS) and antibiotics (100 μg/mL of penicillin/streptomycin mixture) in a humidified atmosphere of 5% $CO_2$ and 37° C. SH-SY5Y cells (human neuroblastoma cells) were cultured in DMEM/F12 supplemented with 10% FBs and antibiotics at 5% $CO_2$ and 37° C.

Example 4

Transduction

Hereinafter, the term 'TAT-MTS-hMT1A' is abbreviated as 'TMhM.'

A synthetic gene of HindIII-TMhM-6xHis-BamHI (Bioneer, Korea) ("6xHis" disclosed as SEQ ID NO: 19) was cloned using pcDNA 3.1 (Progmega). A synthetic gene sequence is as follows (SEQ ID NO: 13):

<u>AAG CTT</u> ATG GGC TAT GGC AGG AAG AAG CGG AGA CAG CGA

CGA CGA TTG TTG CGC GCT GCC CTG CGC AAG GCT GCC CTG

ATG GAC CCC AAC TGC TCC TGC GCC ACT GGT GGC TCC TGC

ACC TGC ACT GGC TCC TGC AAA TGC AAA GAG TGC AAA TGC

ACC <u>TCC</u> TGC AAG AAG AGC TGC TGC TCC TGC TGC CCC ATG

AGC TGT GCC AAG TGT GCC CAG GGC TGC ATC TGC AAA GGG

GCA TCA GAG AAG TGC AGC TGC TGT GCC CAT CAT CAT CAT

CAT CAT TAG <u>GGA TCC</u> pcDNA3-TMhM plasmids were transduced into SK-Hep cells as 70% confluents on 6-well plates containing Superfect® transduction reagents (QIAGEN, Valencia, Calif.). For 2 weeks, stable cells were selected using G418 (1000 μg/mL). Plasmid pcDNA3.1-transduced cells were used as controls. Transduced cells were analyzed via an immunochemical method or Western blot.

Example 5

Production of Zn-TMhM Protein

A synthetic gene of Nco I-TAT-aMTS-HindIII-hMT1A-XhoI (Bioneer, Korea) was cloned using pET28a(+) (Clontech, CA, USA). The synthetic gene sequence is as follows (SEQ ID NO: 14):

<u>CC ATG G</u>GC TAT GGC AGG AAG AAG CGG AGA CAG CGA CGA

CGA TTG TTG CGC GCT GCC CTG CGC AAG GCT GCC CTG GGC

<u>AAG CTT</u> ATG GAC CCC AAC TGC TCC TGC GCC ACT GGT GGC

TCC TGC ACC TGC ACT GGC TCC TGC AAA TGC AAA <i>GAG</i> TGC

AAA TGC ACC TCC TGC AAG AAG AGC TGC TGC TCC TGC TGC

CCC ATG AGC TGT GCC AAG TGT GCC CAG GGC TGC ATC TGC

AAA GGG GCA TCA GAG AAG TGC AGC TGC TGT GCC <u>CTC GAG</u>

For cloning other carrier proteins HindII was inserted between aMTS and hMT1A. pET28a-TMhM plasmid was transformed into an *E. coli* BL21 (DE) pLysS (Novagen, Madison, Wis.), and cultured for 4 hours at 37° C. with 50 μg/mL of ampicillin in an LB medium until $OD_{600\,nm}$ reached 0.4~0.6. In order to induce a protein expression, isopropyl-beta-D-thio-galactoside (IPTG, 1 mM) was added to the medium, and cells were cultured overnight at 26° C. In order to increase the stability of MT1A, 1 mM ZnSO$_4$ (Sigma, St Louis, Mo.) was added during the culture. Cell pellets were collected by centrifugation, and dispersed in a lysis buffer in the presence of 100 mM of phenylmethylsulfonyl fluoride (PMSF). Subsequently, it was sonicated for 30 seconds for 8 times. The supernatant was filtered through a 0.45 µm filter, and purified via immobilized metal affinity chromatography using Ni-NTA resin columns together with FPLC (Bio-Rad, Hercules, Calif.). Zn-TMhM proteins were prepared by removing salts from purified proteins via dialysis using a membrane (Spectrum Laboratories, CA) with a cutoff value of 3,500 mw with respect to phosphate buffered saline of pH 7.4 containing 20% glycerol and 1 mM PMSF. Prior to storing at 4° C., a protease inhibitor cocktail (Roche, Switzerland) was added in the protein preparation.

Zn-TMhM proteins used in the present invention were confirmed as human MT1A via Maldi-TOF/Ms/Ms (FIG. 12).

Example 6

Confirmation of Localization to Mitochondria

In order to test whether TAT-MTS transports hMT1A to mitochondria, His-tag TMhM transduced with plasmids was overexpressed in SK-Hep1 cells. In particular, cells grown on glass cover slips of 6-well plates were treated with 2 µM Zn-TMhM for an hour, and results were analyzed via a Western blot and a confocal laser scanning microscopy.

Isolation of Mitochondria

Mitochondria of SK-Hep1 cells were prepared via differential centrifugation. In particular, cells were obtained and homogenized in 1 mL of a mitochondrial isolation buffer solution (MIB, 0.25M sucrose, 0.025 M Tris, and 1 mM EDTA, pH 7.4). Cell homogenates were centrifuged at 3,000 rpm for 10 minutes, and supernatants were centrifuged at 9,500 rpm for 10 minutes. Mitochondrial pellets were redispersed using MIB, and the protein concentration was analyzed by a BCA method (Pierce, Rockford, Ill.).

Western Blot Analysis

Total cell lysates (30 µg) or mitochondria lysates (10 µg) were isolated by 15% SDS-PAGE, analyzed by a Western blot and enhanced using an electrochemiluminescence system (ECL, Amersham Bioscience, NJ). The primary antibody to 6×His (SEQ ID NO: 19) (1:1000, Cell Signaling Technology, Beverly, Mass.) and the primary antibody to Hsp60 (1:1000, Santa Cruz) were obtained commercially. The HRP-conjugated secondary antibody was purchased at Cell Signaling Technology (Beverly, Mass.). Equivalent protein loading was confirmed by an anti-beta-actin antibody (Sigma Co., St. Louis, Mo.), and results are shown in FIG. 3A.

As shown in FIG. 3A, mitochondria fraction isolated from transduced cells exhibited clear bands of MT1A-6×His ("6×His" discloses SEQ ID NO: 19) on a Western blot.

Confocal Laser Scanning Microscopy

Cells treated with 2 µM Zn-TMhM for an hour were washed with DPBS and stained with MitoTracker Orange (Molecular Proves, Eugene, Oreg.) in a complete medium containing 10% FBS for 20 minutes until the final concentration reached 300 nM. Cells were fixed for 10 minutes using 4% ice-cold paraformaldehyde and permeated using 0.1% Triton X-100. Cells were covered with 5% BSA in Tris-buffered saline for an hour and cultured with rabbit polyclonal 6×His antibodies ("6×His" disclosed as SEQ ID NO: 19) (Cell signaling Technology, Beverly, Mass., USA; 1:500). After washing, cells were detected using secondary antibodies conjugated to Alexa Fluor 488 (1:1000, Molecular Probes). The nucleus was stained with Hoechst (2 µg/mL Molecular Probes, Eugene, Oreg.) in PBS for 5 minutes at room temperature. Then, slides were washed twice with PBS and enhanced in DAKO fluorescence mounting medium (DAKO corporation, Carpinteria, Calif.). Specimens were observed via a confocal laser scanning microscope (Carl Zeiss, Germany) at 405 nm, 488 nm and 555 nm for Hoechst, 6×His (SEQ ID NO: 19), and MitoTracker, respectively, and results are shown FIG. 3B.

As shown in FIG. 3B, immunochemical staining results also confirmed mitochondria localization of overexpressed TMhM-6×his. ("6×His" disclosed as SEQ ID NO: 19). Thus, it was confirmed that artificial TAT-MTS can act as a novel mitochondria targeting sequence, and that TMhM exhibits ability to target mitochondria.

Example 7

Verification of Zn-TMhM Expressed and Purified in *E. coli*

Expression and Purification of Zn-TMhM in *E. coli*

In order to verify its potential as a prodrug of TMhM proteins, Zn-TMhM was expressed in *E. coli* and purified via affinity chromatography. In particular, TMhM proteins were expressed in *E. coli* in the presence of ZnSO$_4$ and purified via Ni-NTA affinity columns. The purity of Zn-TMhM proteins were verified via Coomassie blue staining and a Western blot, and results are shown in FIG. 4A As shown in FIG. 4A, both Coomassie blue staining and Western blot results confirmed the presence and purity of Zn-TMhM.

Verification of Zn-TMhM Localization

Next, Sk-Hep1 cells were cultured with recombinant Zn-TMhM (2 µM) for an hour, and localization of Zn-TMhM was analyzed. Results are shown in FIG. 4B. As a control group, a DPBS-treated group was used.

As shown in FIG. 4B, while cell lysates of Zn-TMhm proteins exist in two different sizes (10.1 kDa and 7.6 kDa) according to a Western blot using His-tag antibodies, mitochondria showed only 7.6 kDa Zn-TmhM.

In addition, to verify whether purified proteins maintain localization in mitochondria in two other kinds of cells (SK-Hep1 and SH-SY5Y), immunocytochemical staining of His-tag Zn-TMhM proteins was performed after Mitotracker staining, and results were observed via a confocal laser scanning microscope (×400, Scale bar=10 µm).

As shown in FIG. 4C, confocal images verified that Zn-TMhM localizes to mitochondria in both SK-Hep1 and SH-SY5Y. This means that extrinsic Zn-TMhM transports MT1A into mitochondria in a short culturing time of an hour, and that TAT-MTS allows protein drugs to effectively permeate cellular and mitochondrial membranes.

Maintaining TAT-MTS Activity in Mitochondria

Sk-Hep1 cells transfected with dsRed2-mito plasmids (dsRed2-mito-SK-Hep1) were prepared as stable cells. These cells allow observation of mitochondria without other treatments. dsRed2-mito-SK-Hep1 cells cultured on cover glass in a 35 mm plate were treated with Tat-aMTS-GFP (TM-GFP) proteins (final concentration of 2 µM) for the times indicated in FIG. 13 (1 hour~72 hours). After the treatment, cells were removed from a medium containing TM-GFP, washed with PBS, added to a medium that does not contain TM-GFP proteins, and cultured again for 24 hours~72 hours. After cover glasses were withdrawn at each treatment time, cells were fixed and observed via a confocal microscopy.

As shown in FIG. 13, TM-GFP proteins were continuously present in mitochondria from 48 hours to 72 hours. It was observed that when TM-GFP proteins were removed from the medium, TM-GFP proteins were present in mitochondria up to 48 hours, but were completely degraded after 72 hours. Results confirmed that a fusion protein including a Tat-aMTS peptide according to the present invention maintains activity for 72 hours and may lose the activity when removed from the system.

Example 8

Verification of Intracellular Processing

Since most MTS are removed from their precursor proteins after being transported to mitochondria, there are high possibilities that TAT-MTS may be processed by TMhM inside mitochondria, as predicted in FIG. 4B (two different sizes are observed: 10.1 kDa and 7.6 kDa). Thus, for verification, molecular weight of transduced MT1A in mitochondria was investigated.

As shown in FIG. 5A, a molecular weight of TMhM proteins inside mitochondria was clearly demonstrated to be 7.6 kDa. Thus, while molecular weight of Zn-TMhM precursors was expected to be 10.1 kDa, molecular weight of a mature form became 7.6 kDa after being processed by a matrix metalprotease which is a mitochondrial matrix signal peptide processing enzyme. Such changes in structure (or length) are demonstrated in FIG. 5B. The arrow indicates a processing site in FIG. 5B, and when Zn-TMhM is processed inside mitochondria, it becomes hMT1A which includes His-tag and amino acid residues (AAGKL) (SEQ ID NO: 18).

Example 9

Verification of Mitochondria Targeting of Various Proteins

In order to verify if TAT-MTS exhibits cell permeability and mitochondria localization even when it is bound to other proteins, in silico analysis was performed. SOD1 which is an intracellular antioxidant protein, catalase, EPX, GPX, PARK2, LRRK2, and PARK2 or LRRK2 which are PD-related proteins were virtually conjugated with TAT-MTS as candidate protein drugs. Mitochondria targeting scores were calculated using MitoProtII.

TABLE 1

| Name | Size (kDa) | Probability | TAT-aMTS Size (kDa) | Probability |
|---|---|---|---|---|
| MT1A | 6.12 | 0.0028 | 8.97 | 0.9709 |
| SOD1 | 15.94 | 0.0101 | 18.79 | 0.9993 |
| Catalase | 66.5 | 0.0616 | 69.35 | 0.9989 |
| EPX | 81.5 | 0.0269 | 83.9 | 0.9979 |
| GPX | 21.94 | 0.4122 | 24.79 | 0.9986 |
| PARK2 | 51.65 | 0.0071 | 54.5 | 0.9995 |
| LRRK2 | 286.15 | 0.0652 | 289 | 0.9996 |

As shown in Table 1, all candidates exhibited almost 100% mitochondria targeting probabilities. Thus, it was observed that a mitochondria targeting sequence according to the present invention exhibits excellent mitochondria targeting activity, independent of substances conjugated (or bounded) thereto, and may be effectively used in drug delivery.

Example 10

Verification of Cell Viability and Effects on Tyrosine Hydroxylase

Cell Viability Assessment (MTT Assay)

MTT analysis is a method for measuring activity of mitochondria dehydrogenase in cells. SH-SY5Y cells on 96-well plates containing DMEM-F12 which consists of 0.5% FBS ($1 \times 10^5$ cells/well) were treated with 1 mM 1-methyl-4-phenyl-2,3-dihydropyridinium ion ($MPP^+$) for 24 hours. Thereafter, cells were cultured with purified TMhM for 24 hours, and cultured with 0.2 mg/mL of 3-(4,5-dimethylthiazol-2-yl)-2,5-diphenyl-tetrazolium bromide (MTT, Sigma Co., St. Louis, Mo.) in PBS solution for 4 hours. MTT formazan precipitates formed by living cells were dissolved in 100 μL of 0.04N HCL/isopropanol. The absorbance was measured at 540 nm using an ELISA microplate reader (Molecular Devices, Sunnyvale, Calif.).

As shown in FIG. 6, treating Zn-TNhM for 24 hours in SH-SY5Y cells increased mitochondrial NADH dehydrogenase activity (MTT) in a dose-dependent manner (FIGS. 6A and 6B). Treatments longer than 48 hours and 72 hours did not alter MTT activity, which indicates that Zn-TNhM sufficiently exhibits the physiological activity even after 48 hours.

Intracellular ATP Measurement

Using an ATP bioluminescent somatic cell assay kit (bioluminescent somatic cell assay kit, Sigma Co., St. Louis, Mo.), the intracellular ATP concentration was measured via a luciferin-luciferase reaction. In particular, 100 μL of cell lysates were mixed with 100 μL of a luciferin-luciferase reaction buffer solution and cultured for 10 minutes at 20° C. Fluorescent signals were measured by a LB 9501 Lumat luminometer (Berthold, Badwildbad, Germany). Signals were calculated after excluding background florescence values of control group wells containing a cell-free medium, and the amount of ATP was normalized to a protein concentration. All data were expressed in % control.

As shown in FIG. 6C, it was confirmed that the treatment of Zn-TMhM increased intracellular ATP contents in a dose-dependent manner.

Verification of Tyrosine Hydroxylase (TB) Expressions

Expressions of tyrosine hydroxylase (TH) which is a restriction enzyme of dopamine synthesis as well as a survival marker for dopminergic neurons was verified by a Western blot. As a control group (CTL), a DPBS-treated group was used.

As shown in 6D, 6×His (SEQ ID NO: 19) and β-actin demonstrated presence of Zn-TMhM and the loading control group, thus confirming that tyrosine hydroxylase expressions were not altered by Zn-TNhM.

Example 11

Verification of Recovery of Mitochondria Activity in Parkinson's Cell Models

Therapeutic effects of Zn-TMhM were investigated using $MPP^+$-induced SH-SY5Y cells. $MPP^+$ is useful in inducing mitochondria damages in dopaminergic neurons to imitate Parkinson's disease. 24 hours before treating Zn-TmhM, MPP+ was treated, and recovery from MPP+-mediated damages was monitored.

As shown in FIGS. 7A and 7B, Zn-TmhM restored MTT activity and ATP contents in a dose-dependent manner. Interestingly, as shown in FIG. 7D, TH expressions were perfectly recovered in 4 µM Zn-TMhM. This means that Zn-TMhM effectively restores activity of dopaminergic neurons and implies that Zn-TMhM is one of strong candidate substances for treating Parkinson's disease.

Example 12

Verification of Mitochondria Targeting Effects in Mice

Whether Zn-TMhM proteins are distributed and targeted to mitochondria when administered to mice was investigated. In particular, Zn-TMhM at a concentration of 2 mg/kg was administered to 57/BL6 mice via an intraperitoneal (IP) injection. Following sacrifice after 24 hours, mitochondria were isolated from liver tissues via differential centrifugation. Liver lysates and mitochondria fractions (liver mito) were investigated via SDS-PAGE and a Western blot. The used antibody was His-Tag (6×His) (SEQ ID NO: 19). β-actin and TOM20 served as the loading control groups for liver lysates and mitochondria fractions, respectively.

As shown in FIG. 8, administered Zn-TMhM was present in liver and mitochondria in liver. Thus, it was confirmed that when Zn-TMhM is administered, it can be effectively delivered to a tissue and transports drugs into mitochondria by targeting.

Example 13

Verification of ROS Effects of Mitochondria Targeting Sequences

In order to verify whether Zn-TMhM proteins restore mitochondria functions, experiments were performed by over-expressing miR-24 on neurons with reduced mitochondria functions. The neurons were treated with Zn-TMhM (0 µM, 0.1 µM, and 2 µM) for 24 hours and stained using 1 µM DCF-DA and 0.5 µM Hoechst 33342 at 37° C. for an hour. Florescence intensity was measured at 485 nm/535 nm for DCF-DA and 355 nm/460 nm for Hoechst 33342. Then, ROS amounts were quantified as a ratio of DCF-DA/Hoechst.

As shown in FIG. 9, it was confirmed that by more than 15%, Zn-TMhM reduced ROS which was increased by about 36% compared to the control group.

Comparative Example 1

As Comparative Example, a mitochondria targeting sequence was produced using TAT, mouse metallothione (MT1), and MTS (ITMVSAL) (SEQ ID NO: 20). A schematic diagram of the sequence is shown in FIG. 10.

Metallothionein (MT), TAT-metallothionein (TMT), and TAT-MTS-metallothionein (TMM) each produced in *E. coli* were treated on ds-Red2-mito-transfected cells for 4 hours (FIG. 10A) and for 24 hours (FIG. 10B). Then, cells were stained with His-Tag antibody and observed via a confocal laser scanning microscopy.

As shown in FIG. 11, MT, TMT, and TMM expressions exhibited almost no change in location, and they were all found in the cytoplasm and distributed mainly in the nucleus after 24 hours.

Example 14

Verification of Therapeutic Effects in Parkinson's Disease Animal Models

Mice Breeding 8-week-old C57BL/6 male mice (19 g-22 g) were obtained, bred to adapt in laboratory animal breeding facilities in the College of Pharmacy at Kyung Hee University for more than a week, and used. Water and food were provided to be freely consumed, and breeding conditions maintained consistent temperature (22±2° C.) and humidity (53±3%). Meanwhile, a light-dark cycle (12 hours) was automatically controlled.

Recovery of Dopaminergic Neurons in MPTP-Induced Parkinson's Disease Animal Models Whether symptoms of Parkinson's disease are recovered by isolated and purified Zn-TMhM proteins is verified by applying MPTP-induced Parkinson's disease animal models. In particular, PD mouse models (acute model, 20 mg/kg/injection, 4 times of intraperitoneal injections at 2-hour intervals) were prepared by injecting MPTP into the abdominal cavity of mice (8 weeks old, n=6). A week after injections, 3 g of Zn-TMhM was administered to right substantia nigra (SN) via a stereotaxic injection. 3 days after Zn-TMhM administration, a behavioral experiment (rotarod test) was conducted, and an experiment involving removing brain tissues was conducted. In particular, a behavioral experiment and a brain-tissue-related experiment were performed as described below.

Therapeutic Effects of Zn-TMhM in MPTP-Induced Parkinson's Disease Animal Models Mice were divided into three groups: Group 1 (control group), Group 2 (MPTP-control group), and Group 3 (MPTP-Zn-TMhM administered group). 6 mice were assigned to each experimental group. 2 days before experiments began, pre-training for a rotarod test was conducted. On the experiment day (7D, Day 7), Group 1 was administered with 10 µL of PBS, and Group 2 and 3 were administered with MPTP (20 mg/kg/injection) via intraperitoneal injections 4 times with 2-hour intervals. A week after injections, Zn-TMhM (3 µg/2 µL PBS) was administered in right substantia nigra via a stereotaxic injection. After 3 days, a rotarod test was conducted again. Treatment conditions, etc., of experimental animals are as shown in Table 2, and conditions in a time series order is as shown in FIG. 14.

TABLE 2

| Mouse Model | | C57BL/6, male, 8 weeks, n = 18 in total (n = 6/group) Acute MPTP-included model | | |
|---|---|---|---|---|
| Groups (N = 6) | 1 | PBS (~10 µL), i.p. | Control | Stereotaxic (~2 µL, PBS) |
| | 2 | MPTP in PBS | MPTP + PBS | Stereotaxic (~2 µL, PBS) |
| | 3 | 20 mg/kg/injection i.p. 4 times at 2 h intervals in a day | MPTP + Zn-TMhM | Stereotaxic (Zn-TMhM 3 µg/2 µL) |

Animals were treated as indicated in Table 2, and behavioral data were obtained via an experiment of FIG. 14. On Day 16 (D16), mice were sacrificed and tissues were collected.

Behavioral Experiment on Parkinson's Disease Animal Models

Sensorimotor coordination was measured in Parkinson's disease animal models and a rotarod test was conducted to monitor hypokinesia.

A rotating apparatus consists of a rotating rod (diameter of 7.3 cm) and 5 sections which allows respectively testing 5 mice at once. Mice were trained on a rotating apparatus twice a day for 2 days (rotating speed during training: 5 rpm on Day 1 and 20 rpm on Day 2). For the actual experiment on Day 3, the rotating speed was increased to 25 rpm. Time that mice endured on a rotating rod was measured, and each mouse was tested 3 times with 3-minute intervals. The maximum measurement time was set to 300 seconds.

Preparation of Brain Tissue Samples and Immunocytochemical Analysis

After conducting a rotarod test, an experiment was performed by anesthetizing mice via an intramuscular injection of Zoletil and removing brain tissues.

Striatum (ST) and SN were dissected from brain tissues removed from 3 mice, and protein lysates were prepared. Tyrosine hydroxylase (TH) expressions were verified via a Western blot.

Furthermore, remaining 3 mice were sacrificed for staining by transcardially administering 4% paraformaldehyde (PBS) and removing brain tissues. Brain tissues were fixed again with 4% paraformaldehyde and immersed in a 30% sucrose solution at 4° C. until they settled on the bottom. Frozen brain tissues were segmented as 30 μm coronal segments using cryostat microtome (CM3000: Leica, Wetzlar, Germany). Segmented tissues were stored after immersing in storage media (glycerin, ethylene glycol, and PBS) at 4° C. for immunocytochemical analysis. Brain segments were put on cover slips, washed with PBS, and treated with 1% $H_2O_2$ (PBS) for 15 minutes to eliminate any existing peroxidase activity. Dehydrated brain segments were reacted with the primary antibody, anti-tyrosine hydroxylase (anti-TH, millipore, Rabbit 1:2000), overnight, and reacted with the secondary antibody, biotinated anti-rabbit IgG, for 90 minutes. Next, the segments were reacted with an avidin-biotin complex solution (Vectastain ABCkit; Vector Laboratories, Burlingame, Calif.) for an hour, and stained using diaminobenzidine. Cytoprotective effects on dopaminergic neurons were verified and quantified by measuring optical density in striatum (ST) and counting TH-positive cells in substantia nigra (SN).

Meanwhile, brains of a few mice in each group were not segmented, but isolated into cortex, cerebellum, striatum (ST) and substantia nigra (SN) respectively and conserved for a Western blot.

Verification of Therapeutic Effects in Parkinson's Disease Animal Models

The experimental results showed that Zn-TMhM injections restored motor abilities which were lost by MPTP intraperitoneal injections, to a level almost over the normal level ($p<0.01$), and that TH expressions which were reduced by MPTP was also recovered to a level close to the normal level when TH expressions in SN and ST tissues were analyzed by a Western blot (FIG. 15A) (*$p<0.05$, ***$p<0.001$).

Results from a Western blot and immunostaining of brain tissues showed that the number of TH-positive neurons which was reduced by MPTP in SN and ST, was recovered by Zn-TMhM injections by over 90%. This confirms the effects of recovering damaged dopaminergic neurons, as well as protection of neurons by pre-treatment of Zn-TMhM (FIGS. 15B to 15D).

From the foregoing, one of ordinary skill in the art to which the present invention pertains could understand that the present invention may be embodied in other specific forms without changing technical concepts or essential features of the present invention. In this regard, the exemplary embodiments disclosed herein are only for illustrative purposes and should not be construed as limiting in all respects. The scope of the present invention shall be construed to include not only the exemplary embodiments but also various alternatives, modifications, equivalent and other embodiments that may be included within the sprit and scope of the present invention as defined by the appended claims.

The invention claimed is:

1. A mitochondria targeting peptide represented by the amino acid sequence of Formula 1 below:

[N-terminus-$X^1$-LR-$X^2$-LRK-$X^3$-C-terminus] (SEQ ID NO: 15),     [Formula 1]

wherein $X^1$ is absent, methionine, alanine, leucine, valine, or isoleucine;

$X^2$ is two identical alanines, leucines, valines, or isoleucines; and $X^3$ is GPRLSRL (SEQ ID NO: 16), GPRLSRM (SEQ ID NO: 17), AA or AAL.

2. The peptide according to claim 1, wherein $X^1$ is absent, methionine, alanine, or leucine (SEQ ID NO: 27).

3. The peptide according to claim 1, wherein $X^2$ is two identical alanines or leucines (SEQ ID NO: 28).

4. The peptide according to claim 1, wherein $X^1$ is leucine and $X^2$ is two identical alanines (SEQ ID NO: 29).

5. The peptide according to claim 1, wherein the peptide is any one of SEQ ID NOS: 1 to 10.

6. A recombinant polynucleotide, wherein a polynucleotide encoding a protein transduction domain, a polynucleotide encoding a peptide of any one of claims 1 to 5, and a polynucleotide encoding an antioxidant protein are sequentially bound.

7. The recombinant polynucleotide according to claim 6, wherein the recombinant polynucleotide comprises a nucleic acid sequence of SEQ ID NO: 13 or 14.

8. An expression vector comprising the polynucleotide of claim 6.

9. A host cell transformed by the expression vector of claim 8.

10. A fusion protein, wherein a peptide of any one of claims 1 to 5 is bound to the carboxyl terminus of a protein transduction domain.

11. The fusion protein according to claim 10, wherein a polyhistidine (poly-His) domain is bound to the carboxyl terminus of the fusion protein.

12. The fusion protein according to claim 10, wherein the protein transduction domain is one or more peptides selected from the group consisting of a transactivator of transcription (TAT) protein of HIV-1 virus, polyarginine, penetratin, PEP-1 peptide, and PEP-2 peptide.

13. The fusion protein according to claim 12, wherein the protein transduction domain is SEQ ID NO: 11 or 12.

14. The fusion protein according to claim 10, wherein an antioxidant is additionally bound to the carboxyl terminus of the peptide.

15. The fusion protein according to claim 14, wherein the antioxidant is superoxide dismutase 1 (SOD1), catalase, eosinophil peroxidase (EPX), glutathione peroxidase 2 (GPX), parkinson disease protein 2 (PARK2), leucine-rich repeat kinase 2 (LRRK2), or metallothionein.

16. The fusion protein according to claim 15, wherein the metallothionein is human metallothionein.

17. A pharmaceutical composition for treating Parkinson's disease comprising the fusion protein of claim 14, wherein the antioxidant is human metallothionein 1A.

18. A method for treating Parkinson's disease comprising administering a pharmaceutical composition for treating Parkinson's disease of claim 17 to a subject.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 1

Leu Leu Arg Ala Ala Leu Arg Lys Ala Ala
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      Mitochondrial targeting peptide
```

```
<400> SEQUENCE: 2

Leu Leu Arg Ala Ala Leu Arg Lys Ala Ala Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 3

Leu Leu Arg Leu Leu Leu Arg Lys Ala Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 4

Leu Leu Arg Leu Leu Leu Arg Lys Ala Ala Leu
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 5

Met Leu Arg Ala Ala Leu Arg Lys Gly Pro Arg Leu Ser Arg Leu
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 6

Leu Arg Ala Ala Leu Arg Lys Gly Pro Arg Leu Ser Arg Leu
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 7

Ala Leu Arg Ala Ala Leu Arg Lys Gly Pro Arg Leu Ser Arg Leu
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 8

Met Leu Arg Ala Ala Leu Arg Lys Gly Pro Arg Leu Ser Arg Met
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 9

Leu Leu Arg Ala Ala Leu Arg Lys Gly Pro Arg Leu Ser Arg Met
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      Mitochondrial targeting peptide

<400> SEQUENCE: 10

Ala Leu Arg Ala Ala Leu Arg Lys Gly Pro Arg Leu Ser Arg Met
1               5                   10                  15

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      Protein transduction domain peptide

<400> SEQUENCE: 11

Tyr Gly Arg Lys Lys Arg Arg Gln Arg Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      Protein transduction domain peptide

<400> SEQUENCE: 12

Tyr Ala Arg Ala Ala Ala Arg Gln Ala Arg Ala
1               5                   10

<210> SEQ ID NO 13
<211> LENGTH: 288
<212> TYPE: DNA
<213> ORGANISM: Artificial Sequence
<220> FEATURE:
<223> OTHER INFORMATION: Description of Artificial Sequence: Synthetic
      HindIII-TMhM-6xHis-BamHI polynucleotide
```

<400> SEQUENCE: 13

```
aagcttatgg gctatggcag gaagaagcgg agacagcgac gacgattgtt gcgcgctgcc      60
ctgcgcaagg ctgccctgat ggaccccaac tgctcctgcg ccactggtgg ctcctgcacc     120
tgcactggct cctgcaaatg caaagagtgc aaatgcacct cctgcaagaa gagctgctgc     180
tcctgctgcc ccatgagctg tgccaagtgt gcccagggct gcatctgcaa agggcatca     240
gagaagtgca gctgctgtgc ccatcatcat catcatcatt agggatcc                 288
```

<210> SEQ ID NO 14
<211> LENGTH: 272
<212> TYPE: DNA
<213> ORGANISM: Artificial Sequence
<220> FEATURE:
<223> OTHER INFORMATION: Description of Artificial Sequence: Synthetic
      NcoI-TAT-aMTS-HindIII-hMT1A-XhoI polynucleotide

<400> SEQUENCE: 14

```
ccatgggcta tggcaggaag aagcggagac agcgacgacg attgttgcgc gctgccctgc      60
gcaaggctgc cctgggcaag cttatggacc ccaactgctc ctgcgccact ggtggctcct     120
gcacctgcac tggctcctgc aaatgcaaag agtgcaaatg cacctcctgc aagaagagct     180
gctgctcctg ctgccccatg agctgtgcca agtgtgccca gggctgcatc tgcaaagggg     240
catcagagaa gtgcagctgc tgtgccctcg ag                                 272
```

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid or absent
<220> FEATURE:
<221> NAME/KEY: MOD_RES
<222> LOCATION: (4)..(5)
<223> OTHER INFORMATION: Any two identical hydrophobic amino acids
<220> FEATURE:
<221> NAME/KEY: MOD_RES
<222> LOCATION: (9)..(15)
<223> OTHER INFORMATION: This region may encompass 'Gly Pro Arg Leu Ser
      Arg Leu,' 'Gly Pro Arg Leu Ser Arg Met,' 'Ala Ala' or 'Ala Ala
      Leu' wherein some positions may be absent
<220> FEATURE:
<223> OTHER INFORMATION: See specification as filed for detailed
      description of substitutions and preferred embodiments

<400> SEQUENCE: 15

```
Xaa Leu Arg Xaa Xaa Leu Arg Lys Xaa Xaa Xaa Xaa Xaa Xaa Xaa
1               5                   10                  15
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Pro Arg Leu Ser Arg Leu
1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Pro Arg Leu Ser Arg Met
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Gly Lys Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Thr Met Val Ser Ala Leu
1               5

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Tyr Gly Arg Lys Lys Arg Arg Gln Arg Arg Met Leu Ser Ala Leu
1               5                   10                  15

Ala Arg Pro Val Gly Ala Ala Leu Arg Arg Ser Phe Ser Thr Ser Ala
            20                  25                  30

Gln Asn Asn
        35
```

-continued

```
<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Tyr Gly Arg Lys Lys Arg Arg Gln Arg Arg Ser Val Leu Thr Pro
1               5                   10                  15

Leu Leu Leu Arg Gly Leu Thr Gly Ser Ala Arg Arg Leu Pro Val Pro
            20                  25                  30

Arg Ala Lys Ile His Ser Leu
        35

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Gly Arg Lys Lys Arg Arg Gln Arg Arg Met Leu Arg Ala Ala
1               5                   10                  15

Leu Ser Thr Ala Arg Lys Gly Pro Arg Leu Ser Arg Leu
            20                  25

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Gly Arg Lys Lys Arg Arg Gln Arg Arg Leu Leu Arg Ala Ala
1               5                   10                  15

Leu Arg Lys Ala Ala Leu
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Gly Arg Lys Lys Arg Arg Gln Arg Arg Leu Leu Arg Leu Leu
1               5                   10                  15

Leu Arg Lys Ala Ala Leu
            20

<210> SEQ ID NO 26
<211> LENGTH: 12
<212> TYPE: PRT
<213> ORGANISM: Homo sapiens
```

```
<400> SEQUENCE: 26

Ser Cys Cys Ser Cys Cys Pro Met Ser Cys Ala Lys
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Ala, Leu or absent
<220> FEATURE:
<221> NAME/KEY: MOD_RES
<222> LOCATION: (4)..(5)
<223> OTHER INFORMATION: Any two identical hydrophobic amino acids
<220> FEATURE:
<221> NAME/KEY: MOD_RES
<222> LOCATION: (9)..(15)
<223> OTHER INFORMATION: This region may encompass 'Gly Pro Arg Leu Ser
      Arg Leu,' 'Gly Pro Arg Leu Ser Arg Met,' 'Ala Ala' or 'Ala Ala
      Leu' wherein some positions may be absent
<220> FEATURE:
<223> OTHER INFORMATION: See specification as filed for detailed
      description of substitutions and preferred embodiments

<400> SEQUENCE: 27

Xaa Leu Arg Xaa Xaa Leu Arg Lys Xaa Xaa Xaa Xaa Xaa Xaa Xaa
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid or absent
<220> FEATURE:
<221> NAME/KEY: MOD_RES
<222> LOCATION: (4)..(5)
<223> OTHER INFORMATION: This region may encompass 'Ala Ala' or 'Leu
      Leu'
<220> FEATURE:
<221> NAME/KEY: MOD_RES
<222> LOCATION: (9)..(15)
<223> OTHER INFORMATION: This region may encompass 'Gly Pro Arg Leu Ser
      Arg Leu,' 'Gly Pro Arg Leu Ser Arg Met,' 'Ala Ala' or 'Ala Ala
      Leu' wherein some positions may be absent
<220> FEATURE:
<223> OTHER INFORMATION: See specification as filed for detailed
      description of substitutions and preferred embodiments

<400> SEQUENCE: 28

Xaa Leu Arg Xaa Xaa Leu Arg Lys Xaa Xaa Xaa Xaa Xaa Xaa Xaa
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (9)..(15)
<223> OTHER INFORMATION: This region may encompass 'Gly Pro Arg Leu Ser
      Arg Leu,' 'Gly Pro Arg Leu Ser Arg Met,' 'Ala Ala' or 'Ala Ala
      Leu' wherein some positions may be absent
<220> FEATURE:
<223> OTHER INFORMATION: See specification as filed for detailed
      description of substitutions and preferred embodiments

<400> SEQUENCE: 29

Leu Leu Arg Ala Ala Leu Arg Lys Xaa Xaa Xaa Xaa Xaa Xaa Xaa
1               5                   10                  15
```